US008092794B2

(12) United States Patent
Calenda

(10) Patent No.: US 8,092,794 B2
(45) Date of Patent: Jan. 10, 2012

(54) PHARMACEUTICAL COMPOSITIONS COMPRISING SODS AND PROLAMINE BASED PEPTIDE FRAGMENTS

(75) Inventor: Alphonse Calenda, Le Plessis Grammoire (FR)

(73) Assignee: Isocell Pharma S.A., Paris (FR)

( * ) Notice: Subject to any disclaimer, the term of this patent is extended or adjusted under 35 U.S.C. 154(b) by 231 days.

(21) Appl. No.: 12/224,908

(22) PCT Filed: Mar. 15, 2006

(86) PCT No.: PCT/IB2006/000577
§ 371 (c)(1),
(2), (4) Date: Sep. 8, 2008

(87) PCT Pub. No.: WO2007/105024
PCT Pub. Date: Sep. 20, 2007

(65) Prior Publication Data
US 2009/0226409 A1    Sep. 10, 2009

(51) Int. Cl.
*A61K 38/44* (2006.01)
*A61K 38/43* (2006.01)
*A61K 36/00* (2006.01)
*C12N 9/02* (2006.01)
*C12N 9/00* (2006.01)
*C12P 21/06* (2006.01)
*C07H 21/04* (2006.01)
*C07K 17/00* (2006.01)
*C07K 16/00* (2006.01)

(52) U.S. Cl. ...... 424/94.4; 424/94.1; 435/189; 435/183; 435/69.1; 536/23.2; 536/23.4; 536/23.1; 536/23.6; 530/350; 530/374; 530/379; 530/389.8

(58) Field of Classification Search ........... 424/94.4, 424/94.1; 435/189, 183, 69.1; 536/23.2, 536/23.4, 23.6, 23.1; 530/350, 374, 379, 530/389.8
See application file for complete search history.

(56) References Cited

U.S. PATENT DOCUMENTS

| 6,045,809 A * | 4/2000 | Postaire et al. ............... 424/400 |
| 6,503,506 B1 * | 1/2003 | Germano ..................... 424/94.3 |
| 2004/0241161 A1 * | 12/2004 | Drijfhout et al. .......... 424/144.1 |

OTHER PUBLICATIONS

Vouldoukis et al., Antioxidant and anti-inflammatory properties of a *Cucumis melo* LC. extract rich in superoxide dismutase activity. J. Ethnopharmacology, 2004, vol. 94: 67-75.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*

* cited by examiner

*Primary Examiner* — Ganapathirama Raghu
(74) *Attorney, Agent, or Firm* — Hoffman & Baron, LLP

(57) ABSTRACT

The present invention relates to pharmaceutical compositions adapted for pharmaceutical administration comprising at least one superoxide dismutase and at least one prolamine based peptide fragment. The invention also relates to certain superoxide dismutases and prolamine based peptide fragments.

19 Claims, 13 Drawing Sheets

Line 1: Tomato cytosolic
Line 2: Human
Line 3: Melon chloroplastic

```
1  M-VKAVAVLN  SSEGVSGTYL  FTQVGVAPTT  -VNGNISGLK
2  MATKAVCVLK  GDGPVQGIIN  FEQKESNGPV  KVWGSIKGLT
3  M-VKAVAVLK  GTSDVEGVVT  LTQ-EDDGPT  SVNVRITGLT
   o    ooo oo        o o         o          o   o oo 1  PGLHGFHVHA  LGDTTNGCMS  TGPHYNPAGK  EHGAPEDEVR
2  EGLHGFHVHE  FGDNTAGCTS  AGPHFNPLSR  KHGGPKDEER
3  PGPHGFHLHE  FGDTTNGCIS  TGAHFNPNKL  THGAPEDEIR
   o oooo o    oo o oo o   o o oo      oo o oo o 1  HAGDLGNITV  GEDGTASFTI  TDKQIPLTGP  QSIIGRAVVV
2  HVGDLGNVTA  DKDGVADVSI  EDSVISLSGD  HCIIGRTLVV
3  HAGDLGNIIA  NADGVAEATI  VDNQIPLSGP  NSVVGRAFVV
   o ooooo     oo  o       o  o o o    oo    oo 1  HADPDDLGKG  GHELSKSTGN  AGGRIACGII  GLQG        (SEQ. ID. NO. 49)
2  HEKADDLGKG  GNEESTKTGN  AGSRLACGVI  GIAQ        (SEQ. ID. NO. 50)
3  HELADDLGKG  GHELSLTTGN  AGGRLACGVV  GLTPV       (SEQ. ID. NO. 51)
   o    oooooo o o o    ooo oo o ooo   o
```

Fig. 4

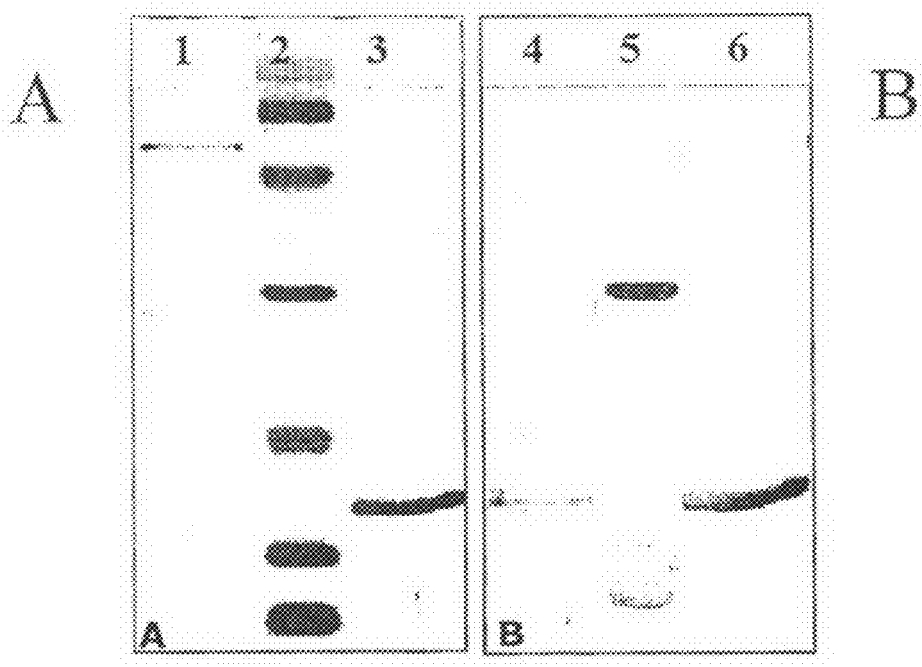
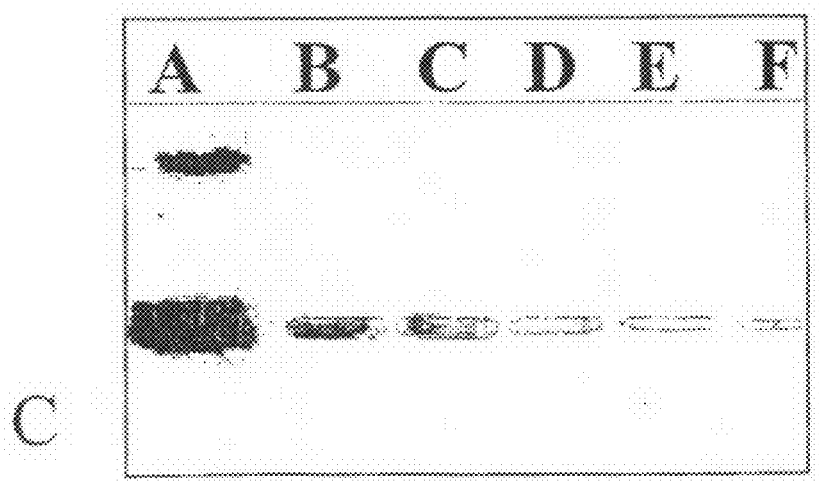
Fig. 7

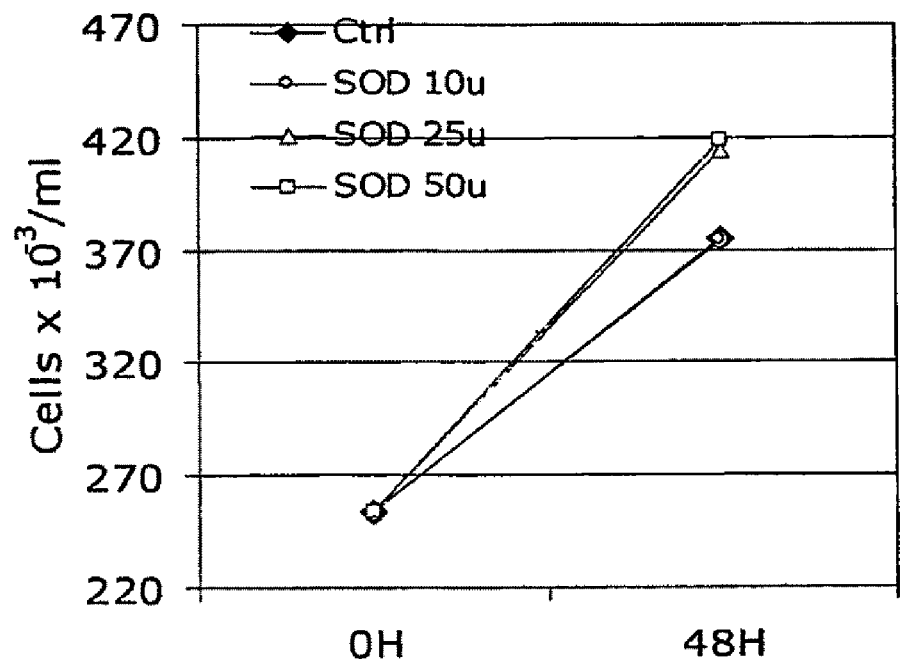
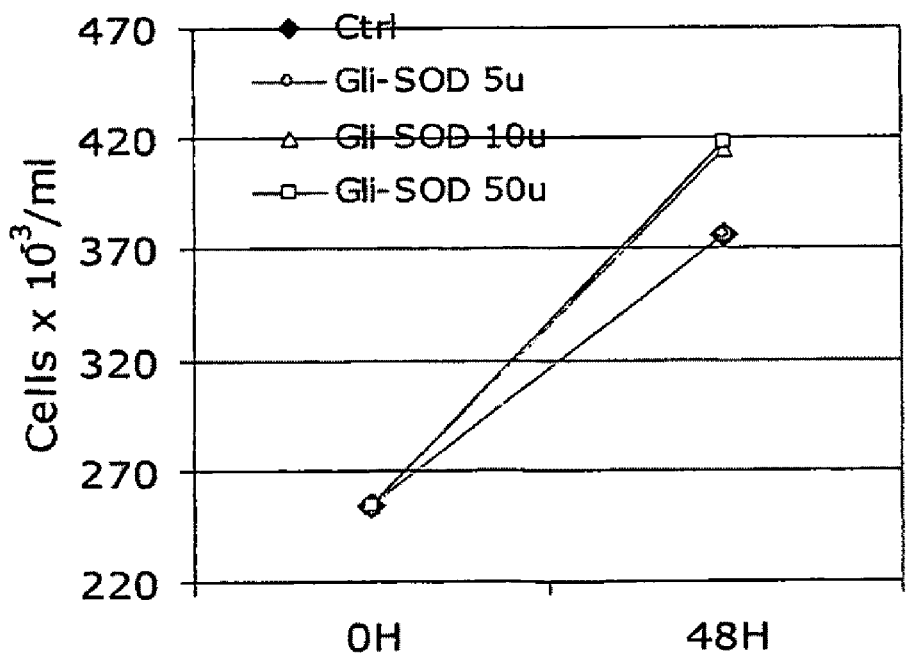
Fig. 9

PHARMACEUTICAL COMPOSITIONS COMPRISING SODS AND PROLAMINE BASED PEPTIDE FRAGMENTS

CROSS REFERENCE TO RELATED APPLICATIONS

This application is the U.S. National Phase of, and Applicants claim priority from, International Application Number PCT/IB2006/000577 filed 15 Mar. 2006, which is incorporated herein by reference.

The present invention relates to pharmaceutical compositions comprising superoxide dismutases, in particular in association with other compounds. The name superoxide dismutase (E.C.1.15.1.1.) or SOD, includes a family of ubiquitous metalloenzymes implicated in the dismutation of the superoxide ($O2$-°) anion. The accumulation or too great a production of the radical species is harmful for most living organisms. This state is still known as oxidative stress, and is associated with a number of metabolic disorders that are themselves involved in various pathological processes such as carcinogenesis, atherosclerosis, aging and inflammatory disorders, such as coeliac disease, also known as gluten intolerance.

Apart from their degree of evolution or the cellular localisation, SOD is present in three main forms that are distinguished by the metal ions contained within the molecule, that is to say copper-zinc or CuZn-SOD, manganese or Mn-SOD and iron or Fe-SOD. CuZn-SOD and Mn-SOD are also to be found in the more specialized cellular structures such as the peroxisomes or the chloroplasts in plants, whereas in mammals, an extra-cellular CuZn-SOD or Ec-SOD has been specifically found in the extra-cellular compartment. More recently, a Ni-SOD having only weak homology to the other known SODs has been identified in *Streptomyces*.

Many experiments have shown that even if all of the SODs have the same antiradical activity, their effective biological activity is not identical with respect to a given therapeutic indication and target organism. In particular, the anti-inflammatory activity of homologous SODs in foot oedema induced by carrageenan or adriamycin in the rat is non functional compared to that of SODs of heterologous origin. The effectiveness of heterologous SODs seems to be more dependent on variations, even subtle ones, in the amino acids of the enzymes rather than in the type of metal present at the active site or the global molecular mass of the enzyme.

Nevertheless, the border that separates a heterologous SOD from an immunogenic SOD has to be determined for each one depending on the heterologous context in which they are used. Indeed, studies in rats have indicated:
  (a) that homologous rat CuZn-SOD or certain heterologous SODs, such as the human Mn-SOD have no anti-inflammatory activity,
  (b) certain heterologous SOD such as bovine CuZn-SODs have such an anti-inflammatory activity and that still others, notably yeast CuZn-SODs, can even have pro-inflammatory activity.

From the various different studies carried out, it has been shown that, even at clinical doses, the homologous type enzymes remain less efficient and that therefore human SOD is far less active than heterologous SODs for certain anti-inflammatory indications in man. For these reasons especially, bovine CuZn-SOD has been shown to exert beneficial effects in clinical trials where it was administered before the onset of Bovine Spongiform Encephalitis (BSE).

In spite of the 18.3% divergence that exists between bovine CuZn-SOD and human CuZn-SOD, and having regard to the large number of injections involved, only very few rare cases of hypersensitivity or anaphylactic shock have been observed. Some earlier work, that was continued later, suggested that the pharmacological activity of heterologous SODs could be progressively inhibited by increasing the rate of circulating anti-SOD antibody. Other, more recent reports, tend to indicate that these circulating antibodies are involved in a process facilitating the presentation and internalisation of the heterologous SOD. Oral administration of SODs is also problematic in that they are often rapidly degraded in the gastrointestinal tract, thus leading to reduced bioavailability, and efficacy. This problem is compounded by the difficulty of getting the SODs to the particular cell location where they will be the most effective.

The applicant has discovered that it was possible to make pharmaceutical compositions comprising at least one superoxide dismutase and at least one prolamine based peptide fragment that solve, among others, said difficulties, and that this association also makes it possible to facilitate cellular targeting of the SOD to the cell locus for optimum efficacy.

Accordingly, it is an object of the present invention to provide a pharmaceutical composition adapted for pharmaceutical administration comprising a functionally active combination of at least one superoxide dismutase (SOD) and at least one prolamine based peptide fragment. By the term "functionally active combination", it is to be understood that the two components described above, either associated or physically or chemically bound to each other, act together to create a synergistic effect over and beyond the mere cumulative effects of each component. In particular in the present invention, it has been found that association of an SOD with a prolamine based peptide fragment, has been found to enhance the duration of the presence of SOD whilst at the same time significantly diminishing any inflammatory response optionally caused by the prolamine-based peptide fragment.

Other objects of the invention will become apparent throughout the description, but particularly preferred objects also include the amino acid molecules incorporated in the pharmaceutical compositions, any nucleic acid sequences coding therefor or obtained via hybridisation, and use of such amino acid molecules as medicaments, as anti-cell stress agents, or for the preparation of a medicament in the treatment of inflammatory pathologies. The invention also covers certain antibodies used to detect the presence of certain prolamine based peptide fragments or their chemical or physical combination with at least one superoxide dismutase. Where reference is made to the term "chimeric", in the claims or in the description, this term means that the molecule contains components originating from two or more distinct genetic sources.

Suitable Prolamines

Preferably, the at least one prolamine based peptide fragment is a fragment of gliadin or a derivative, analog, salt or metabolite thereof. Even more preferably, the prolamine based peptide fragment is a non-immunogenic analog of gliadin. In a most preferred embodiment, the prolamine based peptide fragment is a non-immunogenic analog of gliadin having competitive inhibiting activity with respect to immunogenic prolamine based peptides.

In another preferred embodiment of the invention, the at least one prolamine based peptide fragment is chosen from the group consisting of fully hydrolyzed, substantially hydrolyzed or slightly hydrolyzed prolamine based peptide fragments. In general, however, the at least one prolamine based peptide fragment is chosen from the group consisting of those fragments obtained from PTC (pancreatin, trypsine, chymotrypsin) hydrolyzed prolamine mimicking the gastro-intestinal hydrolyses processes.

In an alternative, but also preferred embodiment, at least one prolamine based peptide fragment is hydrolyzed to the extent that it acts as a targeting signal within the intestinal tract.

Suitable SODs

The superoxide dismutases can be chosen from those generally known to the skilled person, and may be chosen from the group consisting of human superoxide dismutases, animal superoxide dismutases, bacterial superoxide dismutases, yeast superoxide dismutases and plant superoxide dismutases. Preferably however, the at least one superoxide dismutase is selected from the group consisting of CuZn superoxide dismutases, Mn superoxide dismutases, extra-cellular superoxide dismutases, Ni superoxide dismutases, and Fe superoxide dismutases. In one preferred embodiment of the invention, the at least one superoxide dismutase is a homologous superoxide dismutase. In another preferred embodiment of the invention, the at least one superoxide dismutase is a heterologous superoxide dismutase. The term "homologous" refers to the SOD being of the same origin as the native molecule in any given target host for that molecule, and the term "heterologous" refers to the SOD being of different origin to the native molecule in any given target host for that molecule.

In a most preferred embodiment, the at least one superoxide dismutase is a heterologous CuZn superoxide dismutase.

As mentioned previously, the at least one superoxide dismutase is preferably a plant superoxide dismutase, and even more preferably a heterologous CuZn plant superoxide dismutase. Such a superoxide dismutase can be obtained or produced in many different ways. For example, the at least one superoxide dismutase can be extracted from plants. If plants are used for the extraction or production of the at least one superoxide dismutase, these plants can be members of the Cucurbitaceae family, and be preferably selected from the group consisting of melon or alternatively of the Solanaceae family and be preferably selected from the group consisting of tomato.

Among the various plant superoxide dismutases available, the superoxide dismutase according to the invention is preferably selected from the group of plant superoxide dismutases consisting of peroxisomal, chloroplastic and cytosolic superoxide dismutases.

In another preferred embodiment, the at least one superoxide dismutase is a recombinant superoxide dismutase, that can be obtained through genetic engineering and expression in a host cell transformed with a nucleic acid coding for said SOD. In particular, the applicants have found particularly preferable when the at least one superoxide dismutase is a modified chloroplastic, peroxisomal or cytosolic CuZn recombinant superoxide dismutase. In still yet another preferred embodiment, the at least one superoxide dismutase is a hybrid heterologous/homologous superoxide dismutase, preferably a hybrid plant/human superoxide dismutase.

Techniques for introducing foreign or native genes into host cell genomes are well known to the skilled person, as is the expression of recombinant proteins in general. Accordingly, in one preferred embodiment of the invention, the modified chloroplastic, peroxisomal or cytosolic superoxide dismutase is coded by a modified nucleic acid sequence, expressed in a host cell. The general techniques of PCR amplifications involved to obtain these modified coding sequences are also known to the skilled person and do not need to be described here.

In a most preferred embodiment of the invention, the at least one superoxide dismutase is a recombinant superoxide dismutase that is coded by:
a nucleic acid sequence according to any one of the nucleic acid sequences identified as SEQ.ID 24 to SEQ.ID 33;
a nucleic acid sequence hybridising under stringent conditions to any of the nucleic acid sequences identified as SEQ.ID 24 to SEQ.ID 33;
a nucleic acid sequence having at least 70% BLAST identical homology to any one of the sequences identified as SEQ.ID 24 to SEQ.ID 33.

By hybridising under stringent conditions, it is to be understood that the nucleic acid in question will hybridise to the sequences mentioned under the following conditions SSPE× 0,2 at 65° C.

Finally, another object of the invention relates to the use of a pharmaceutical composition as described previously, for the manufacture of a medicament for the treatment of oxidative and inflammatory pathologies or disorders, especially those that accompany most diseases, including gluten intolerance, and preferably coeliac disease.

Heterologous Plant SODs

The applicant has discovered that plant derived SODs are very advantageous in the present invention. CuZn-SODs exist in several forms in photosynthetic cells of higher plants. They are mainly found in chloroplasts and to a lesser degree in the cytoplasm and peroxisomes. They differ from each other in amino acid composition, molecular weight, isoelectric point and their degree of polymerization.

Many of them have been biochemically or genetically characterised. The chloroplastic or peroxisomal plant SODs are firstly produced as a precursor containing a leader sequence or signal peptide at the N-terminal of the protein. This precursor, after translocation into the chloroplasts or the peroxisomes, undergoes functional maturation that consists in the elimination of the extra N-terminal part.

In addition to this specificity, the peroxisomal SODs, particularly those of melon, or the chloroplastic SODs, particularly those of tomato, are (a) better conserved between themselves than the cytosolic SODs, at around 90% conserved regions in the chloroplastic and peroxisomal SODs versus 70% conserved regions in the cytosolic SODs; (b) more resistant, than other plant CuZn-SODs, to heat and hydrogen peroxide inactivation, yet they have never been considered for therapeutic applications, either for enteral or parenteral administration.

Sequence alignment by the applicant has revealed however that chloroplastic or peroxisomal SODs are 2-4% less divergent from human or bovine SOD than their equivalent cytosol derived plant SODs.

In one of the preferred embodiments of the invention, the choice of a chloroplastic CuZn-SOD, for example from melon, was retained by the applicant since certain codons of plant origin that are abundant in the cytosolic forms were identified as rare in bacteria and that for this reason, the expression level, as well as the specific activity of the biosynthetic enzymes that contain them in abundance or at active sites, are significantly modified.

The applicant chose preferably to use a bacterial system as the host cell for recombinant expression of the biosynthetic SODs, and this enabled these two aspects to be verified.

Human CuZn-SOD was expressed and was functional in the applicant's bacterial system. Even though it contains at least two of the rare codons, the two arginine residues that are formed therefrom, which can be found in the N-terminal region, do not appear to be involved in enzymatic functioning of the human SOD.

On the other hand, in the cytosolic tomato SOD, the two arginine residues resulting from the rare codons are located in the C-terminal part of the enzyme, one of them being involved in the enzymatic functioning pertaining to attraction of the superoxide anion.

In this case, the biosynthetic tomato cytosolic SODs expressed in this system are a lot less active. Other work carried out on chloroplastic tomato SOD, in which no such rare codons are present, shows that its expression in bacteria results in a completely functional biosynthetic SOD that is totally active.

The first two melon SODs cloned and expressed in this bacterial system have been shown to have a specific activity similar to that of cytosolic tomato at the level of purification obtained. In this case, the rare codons cover the same positions as those identified in the cytosolic tomato SOD, with one of the arginines being responsible for attraction of the superoxide.

It was therefore advantageous to substitute the currently used host strains by a strain that contains the additional tRNAs for codons rarely used in *E. coli*, i.e. arginine AGG or AGA. This specific strain is designed in order to enhance the expression of functionally active plant proteins in bacteria. The plant origin of the mature SODs, in their extracted form and preferably as a recombinant enzyme, in conjunction with oral administration is therefore able to reconcile both heterologous activity and immunity tolerance, and can thus serve as a substitute for bovine SOD in the treatment of pathological inflammatory processes.

Oral Administration and Cellular Targeting of SODs.

In order to increase the activity of therapeutically acceptable SODs, several different formulations were considered: liposome encapsulation, albumin conjugation, or association with polyethylene glycol, or even the association as a hybrid with heparin affinity peptides.

The anti-inflammatory activity of heterologous bovine CuZn-SODs administered orally, using liposomes or ceramides, was first shown in the reduction of rat leg oedema induced by carrageenan. It was also shown that substituting ceramides with plant prolamines like gliadin, and non recombinant bovine SOD with non recombinant plant SOD, confirmed therapeutic activity that was comparable to injectable bovine SOD in delaying the onset of cognitive disorders induced in rats.

Side Effects of Gliadin Use

There remains however a significant side effect with this type of oral administration for a limited, but non negligible population of sufferers. It is well known that certain substances that were used in the above modified formulation, especially the plant prolamines, like gliadin, can lead to poorly tolerated products after pepsin-trypsin hydrolysis in the gastrointestinal tract, causing gluten allergies, or may even be toxic, as is the case in coeliac disease. This human-only illness is linked to a particular capacity of the brush type edge of human enterocytes to express HLA class II molecules. Some haplotypes, like HLA-DR, and HLA-DP, as well as HLA-DQ, have been shown to be strongly involved in the activation of gliadin-specific T cells. This toxic processing of gliadin peptides is believed to involve three successive steps: a) binding of the toxic fragments of gliadin to HLA receptors and transport into the enterocytes on the edge of the intestinal microvillii;

b) transport to the enterocyte basolateral level where they are presented to CD4+ type intra-epithelial cells in the lamina propria;

c) finally, the intact or partially hydrolyzed polypeptides are released from the enterocyte basolateral membrane towards APC cells (Antigen Presenting Cells) in the lamina propria.

Gliadin peptides present in *Triticum vulgare* and those produced by hydrolysis in the gastro-intestinal tract lead to a negative response, that is, an inflammatory response, whereas when associated with enzymatically active SOD, the negative effects of such peptides are greatly reduced. In addition, it has been discovered that the association of gliadins present in *Triticum durum*, which behave like those present in *Triticum vulgare*, except for the negative side effects mentioned above, has been found to be most preferred when associated with enzymatically active SOD for the treatment of deficiencies that involve an oxidative stress.

Under physiological conditions, the response to antigens presented by epithelial cells is mediated by TH2 type T cells. These cells are responsible for IgA production and, among others, immunity tolerance with regard to food antigens. In the case of gluten intolerance or its more severe form of coeliac disease, the peptides that are derived from gliadin are capable of altering the oxidative metabolism of the enterocytes by generating a state of oxidative stress, which are all the more sensitive to gliadin since they are already in a pro-oxidative state.

This inflammatory state is characterized by a conversion of the cellular response towards the TH1 cell types, in conjunction with important modifications in the production of cytokines and nitrogen monoxide (NO). Under these conditions, an increase in lipid peroxidation as well as in the ratio of the oxidized and reduced forms of glutathione (GSSG/GSH) has reinforced the applicant's hypothesis that the fusion of antioxidants to gliadin should have a beneficial effect in this therapeutic indication.

As a corollary, potentiation of SOD anti-inflammatory activity by the oral route, resulting from its combination with gliadin, would appear to be due to increased affinity for cellular membranes and the underlying control of the associated metabolic pathways.

Thus in order to demonstrate these effects, an enzymatically active heterologous SOD was first associated with a derivative of the hydrolysis product of *Triticum vulgare* prolamines, and in particular of Vul-gliadin, the amino acid sequence of which was confirmed to be Nter-QQPYPQPQPF-Cter (SEQ.ID No. 01), and then with its non toxic analogous derivative of the hydrolysis product of *Triticum durum* prolamines, and in particular of Durgliadin, the amino acid sequence of which was determined to be Nter-QQPQDAVQPF-Cter (SEQ.ID No. 02). This analog is a competitive inhibitor of the toxic derivatives of gliadin, and is capable of targeting their site of interaction with the enterocytes.

The prolamines, and in particular the gliadins, play an active role in protecting the active components they surround during gastrointestinal transit, and in their hydrolyzed form favour targeting and progressive release of the active components at cells within the intestinal mucous membranes. When these derivatives are substituted with a non-toxic analog added to the N-terminal part of a protein, for example a heterologous SOD, it is possible to maintain the derivative peptide fragment's role as an enterocyte targeter and at the same time avoid the deleterious effects of the antigenic derivatives of the prolamines.

In view of the pharmacological efficacy demonstrated by injectable bovine SOD in several therapeutic indications, but also of the problems of public safety generated by the arrival of BSE and CFJD, the objects of the invention described above are found to have the following advantages:

1. a heterologous non-immunogenic SOD, or one that only induces immunity tolerance, irrespective of the genetic background of the recipient;
2. a plant derived SOD, advantageously of food origin
3. a formulation making heterologous SODs pharmacologically active through an administrative route traditionally known to be ineffective for such SODs;
4. and coupling of this heterologous SOD with a non-toxic intestinal targeting peptide, thereby reinforcing the heterologous activity of these SODs administered orally and representing a therapeutic alternative in indications that as yet have no treatment, in particular for orphan drug indications.

These and other embodiments of the present invention will be described in detail hereafter.

BRIEF DESCRIPTION OF THE FIGURES

FIG. 4 is a representation of the amino acid alignment of three different Cu—Zn superoxide dismutases from varying origins, in particular a tomato cytosolic SOD (line 1), a human SOD (line 2), and a melon chloroplastic SOD (line 3). The identities of amino acid residues between the sequences are indicated beneath each group of three SODs via a circle;

FIG. 6 is a representation of the folding of recombinant SOD or Gli-SOD respectively using NBT reduction gel electrophoresis, in which:
  FIG. 6A shows rec SOD with lanes A and A' being loaded with 125 µg of natural melon extract (equivalent to 90 U/mg), and lanes 1,1', and 1''' being loaded with 0.92 µg of native SOD;
  FIG. 6B shows rec Gli-SOD according to the invention with lanes A and A' being loaded with 125 µg of natural melon extract (equivalent to 90 U/mg), lanes 1 and 1' being loaded with 1.84 µg of recombinant Gli-SOD, and lanes 2 and 2' being loaded with 0.92 µg of recombinant Gli-SOD;

FIG. 7 is a SDS-PAGE of the following:
  FIG. 7A represents the Coomassie blue revelation of:
    50 µg of natural *Cucumis melo* extract in lane 1
    Protein markers in lane 2 (6.6, 14.1, 21.1, 31, 45 and 67 KDa);
    2.5 µg of bovine SOD (Sigma) in lane 3
  FIG. 7B represents EP1669 antibody revelation with 50 µg of natural *Cucumis melo* extract in lane 4;
    Protein markers in lane 5 (6.6, 14.1, 21.1, 31, 45, 67 KDa)
    2.5 µg of bovine SOD (Sigma) in lane 6.

FIG. 9 is a graphical comparison of the minimal effective dose of rec SOD or rec Gli-SOD according to the invention where N=4;

FIG. 11A is the negative control, FIG. 11B is after treatment with rec SOD, and FIG. 11C is after treatment with rec Gli-SOD, where the white areas indicate presence of the SOD in the vicinity of the cell;

FIG. 12A represents the results obtained using 10 U, and FIG. 12B the results obtained using 50 U, of the rec SOD and rec Gli-SOD respectively;

DETAILED DESCRIPTION OF THE INVENTION

EXAMPLES

Example 1

Figure 2:
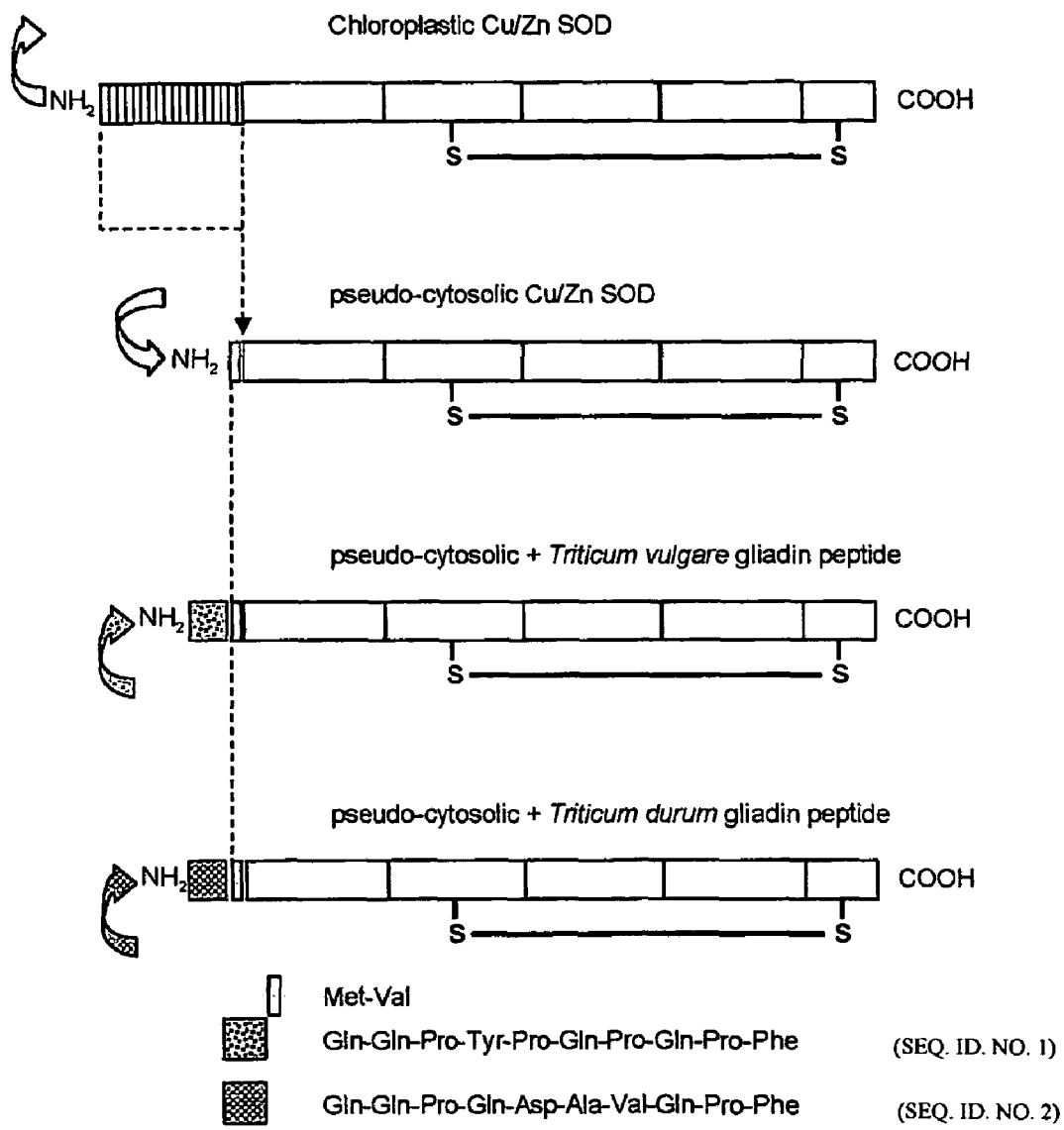
FIG. 2 is a schematic representation of the general scheme of genetic engineering undertaken to produce the recombinant and chimeric SOD molecules of the present invention.
Figure 3:
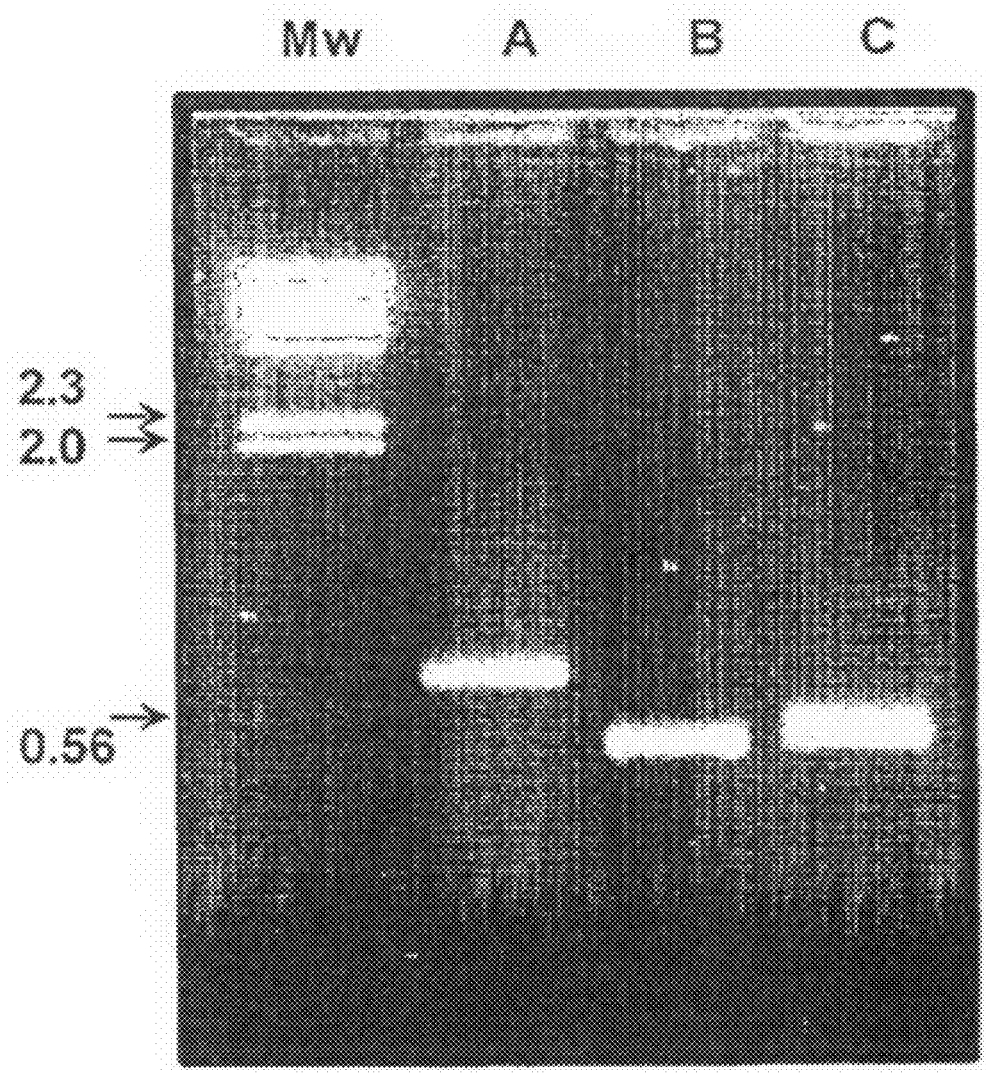
FIG. 3 represents an agarose gel electrophoresis obtained from the RT-PCR amplifications of various melon Cu—Zn SOD variants according to the invention, in particular where run A is a recombinant chloroplastic melon Cu—Zn SOD, run B is a recombinant melon pseudo-cytosolic Cu—Zn SOD, and run C is the recombinant pseudo-cytosolic Cu—Zn SOD of run B bearing an N-terminal fusion to a gliadin peptide.

Cloning of a messenger RNA that codes for the copper-zinc peroxisomal or chloroplastic superoxide dismutase obtained from melon <<*Cucumis melo* L>> and the determination of its complete nucleic acid sequence (both coding and untranslated sequences) was undertaken by sequential RT-PCR amplifications. A first clone containing only the coding sequence was modified by genetic engineering, in order to obtain a first protein variant named Pseudo-Cytosolic, as illustrated in FIG. 2, that represents the general scheme of genetic modifications for melon chloroplastic SOD. This first variant shows a replacement of the first 65 amino acids at the N-terminus, corresponding to the native signal peptide, with the amino acid pair methionine-valine that is characteristic of the N-terminal of cytosolic plant SODs. This technologically engineered process reproduces the chloroplastic maturing step that SODs undergo in the plant cell, followed by the addition of the two amino acids indicated. The second and the third variants contain respectively, in addition to this methionine-valine amino acid pair, the gliadin peptide sequence for gastrointestinal targeting (Nter-QQPYPQPQPF-Cter (SEQ.ID No. 01), referred to as Vul), the origin of which is *Triticum vulgare*, and the peptide sequence which will enable reproduction of the gliadin peptide interactions on enterocytes without generating a sensitising response, as follows: (Nter-QQPQDAVQPF-Cter (SEQ.ID No. 02), referred to as Dur), the origin of which is *Triticum durum*.

Example 2

Cloning of a messenger RNA that codes for the copper-zinc SOD cytosolic superoxide dismutase was obtained from tomato leaves *Lycopersicon esculentum* (PubMed Blast Accession number X14040) by direct RT-PCR amplification of the entire coding sequence to give rise to the first tomato variant named cytosolic. The second and the third variants were also genetically modified by addition of the gliadin peptide sequence for gastrointestinal targeting (Nter-QQPYPQPQPF-Cter (SEQ.ID No. 01), referred to as Vul), the origin of which is *Triticum vulgare*, and the peptide sequence which will enable reproduction of the gliadin peptide interactions on enterocytes without generating a sensitising response, as follows: (Nter-QQPQDAVQPF-Cter (SEQ.ID No. 02), referred to as Dur), the origin of which is *Triticum durum*.

Example 3

Cloning of a messenger RNA that codes for the copper-zinc SOD cytosolic superoxide dismutase obtained from human blood cells *Homo sapiens* (PubMed/Blast Accession number K00065) by direct RT-PCR amplification of the entire coding sequence to give rise to the first human variant named cytosolic. The second and the third variants were also genetically modified by addition of the gliadin peptide sequence for gastrointestinal targeting (Nter-QQPYPQPQPF-Cter (SEQ.ID No. 01), referred to as Vul) and the peptide sequence which will enable reproduction of the gliadin peptide interactions on enterocytes without generating a sensitising response, as follows: (Nter-QQPQ-DAVQPF-Cter (SEQ.ID No. 02), referred to as Dur).

Example 4

The expression products of the first variants for each kind of constructions were used to validate the anti-radical activity of the various biosynthetic SODs obtained. These activities were verified by the reduction of NBT on native PAGE. The results show that the activities of the recombinant biosynthesized proteins are very closely linked to the presence in the plant cDNA, of codons that are rarely present in the most currently used bacterial host strains of today.

The low rate of expression or activity from the three cDNA expressed in the currently used strains of today may be explained by the presence of codons rarely used by the bacterial strains notably the codons AGA, AGG (arginine), and to a lesser extent, the codons CCC (proline), GGA (glycine) CTA (leucine), and ATA (isoleucine). In order to circumvent this problem, the cDNA were transferred into another expression vector system, identified as pET30a+ (available from NOVAGEN) and used to transform a permissive bacterial strain identified as Rosetta DE3 pLysS (available from NOVAGEN), which contains the appropriate tRNAs for these rare amino acids.

DETAILED PROTOCOLS OF THE INVENTION

Cloning protocol and genetic modification of *Cucumis melo* L SOD.

Total RNA was extracted from nitrogen cryostored *Cucumis melo* L melon leaves, either from the variety *cucumis melo* L (commercial variety registered as VILMORIN-GNIS-2251029), or from the variety *cucumis melo* LC (variety registered as ASL-NCIMS-40310), using a technique identical to that used for eukaryotic cells [TRIzol-TM kit, Life Technologies, France].

3'RACE-PCR of Melon SOD

The transcription of the messenger RNA into a single stranded DNA matrix was carried out from a modified oligo dT primer AAGCAGTGGTATCAACGCAGAG-TACTTTTTTTTTTTTTTTTTTTTTTTTTTTTTVN (SEQ.ID No. 03) [Clontech, Smart cDNA ref:k1051] in 25 µl of reaction buffer: Tris HCl 20 mM pH8.3, KCl 50 mM, MgCl$_2$ 2.5 mM, 10 mM DTT and 400 µM of each of the dNTP in the presence of 200 units of Superscript II reverse transcriptase (Gibco-BRL) for an hour at 42° C.

Amplification of the 3' extremity of the messenger RNA coding for SOD was effected by combining several single stranded primer pairs such as the Endprimer AAGCAGTG-GTATCAACGCAGAGT (SEQ.ID No. 04), as the complement to the modified oligo dT primer, and respectively Melcyt5F1 GGTGAYACMACMMTGGYTG (SEQ.ID No. 05) and Melcyt5S2 CATGCKGGKGAYCTDGG (SEQ.ID No. 06) for the melon coding region. The amplimer sequences are by their nature very degenerate, since they are based on conserved regions of the peroxisomal, chloroplastic and cytosolic CuZn-SODs of several plant species.

5' RACE-PCR of Melon SOD

After cloning into a bacterial vector pGEM-T (available form Promega), 7 independent clones were sequenced and the consensus sequence used to construct three new specific primers Ved3R3 ACAAAGGCTCTTCCAACTACAG (SEQ.ID No. 007), Ved3R2 GCCGCTAAGAGGAATCTG (SEQ.ID No. 08) and Ved3R1 TGGTTGCCTCTGCTACTC-CATC (SEQ.ID No. 09). The specific primer Ved3R3 was used to transcribe the messenger RNA into a single stranded DNA matrix, terminated by a dCTP homopolymeric elongation (5'RACE system, Life Technologies, ref: 18274-058). The amplification of this matrix was obtained through the successive combination of the primer AAPP GGCCAG-GCGTCGACTAGTACGGGGGGGGGGGGGGGG (SEQ.ID No. 10) and Ved3R2 for the pre-amplification step and then AAP GGCCAGGCGTCGACTAGTAC (SEQ.ID No. 11) and Ved3R1 for final amplification of the 5' extremity of the specific messenger RNA.

Amplification and Genetic Modification of the Three SOD Variants

The amplification of the different SOD variants from each species: human, tomato and melon, was enabled by the combination of three single stranded 5' amplifiers with a unique single stranded 3' amplimer for each species, as follows:

| Name | Site | Sequence |
|---|---|---|
| Hum5Cyt | NcoI | atcggatccATGGCGACGAAGGCCGTGTGCGTG (SEQ. ID No 12) |
| Hum5Dur | NcoI | atcggatccATGGCTCAACAACCACAAGATGCTG TCCAACCATTCATGGCGACGAAGGCCGTGTGCGT G (SEQ. ID No 13) |
| Hum5Vul | NcoI | atcggatccATGGCTCAACAACCATATCCACAAC CACAACCATTCATGGCGACGAAGGCCGTGTGCGT G (SEQ. ID No 14) |
| Hum3Rfw | HindIII | ctcgagaaqcttTTATTGGGCGATCCCAATTAC (SEQ. ID No 15) |
| Tom5Cyt | NcoI | atcggatccATGGTGAAGGCCGTCGCCGTCCTT (SEQ. ID No 16) |
| Tom5Dur | NcoI | atcggatccATGGCTCAACAACCACAAGATGCTG TCCAACCATTCATGGTGAAGGCCGTCGCCGTCCT T (SEQ. ID No 17) |
| Tom5Vul | NcoI | atcggatccATGGCTCAACAACCATATCCACAAC CACAACCATTCATGGTGAAGGCCGTCGCCGTCCT T (SEQ. ID No 18) |
| Tom3Rfw | HindIII | ctcgagaagcttTAACCCTGGAGGCCAATAAT (SEQ. ID No 19) |

-continued

| Name | Site | Sequence |
|---|---|---|
| Mel5pCyt | NcoI | atcggatccATGGTGAAAGCTGTCGCTGTCCTC (SEQ. ID No 20) |
| Mel5Dur | NcoI | atcggatccATGGCTCAACAACCACAAGATGCT GTCCAACCATTCATGGTGAAAGCTGTCGCTGTCC TC (SEQ. ID No 21) |
| Mel5VuI | NcoI | atcggatccATGGCTCAACAACCATATCCACAAC CACAACCATTCATGGTGAAAGCTGTCGCTGTCCT C (SEQ. ID No 22) |
| Mel3Rfw | HindIII | ctcgagaagcttCACACAGGAGTCAGACCGAC (SEQ. ID No 23) |

Where Cyt designates the melon pseudo-cytosolic form comprising the two additional amino acids, instead of the original 65 amino acid sequence, and for the cytosolic forms in human and tomato. The references Dur and Vul indicate respectively:
DUR for the cytosolic forms comprising the gastrointestinal targeting signal peptide taken from *Triticum durum*,
VUL for the cytosolic forms comprising the gastrointestinal targeting signal peptide taken from *Triticum vulgare*.

Figure 1:
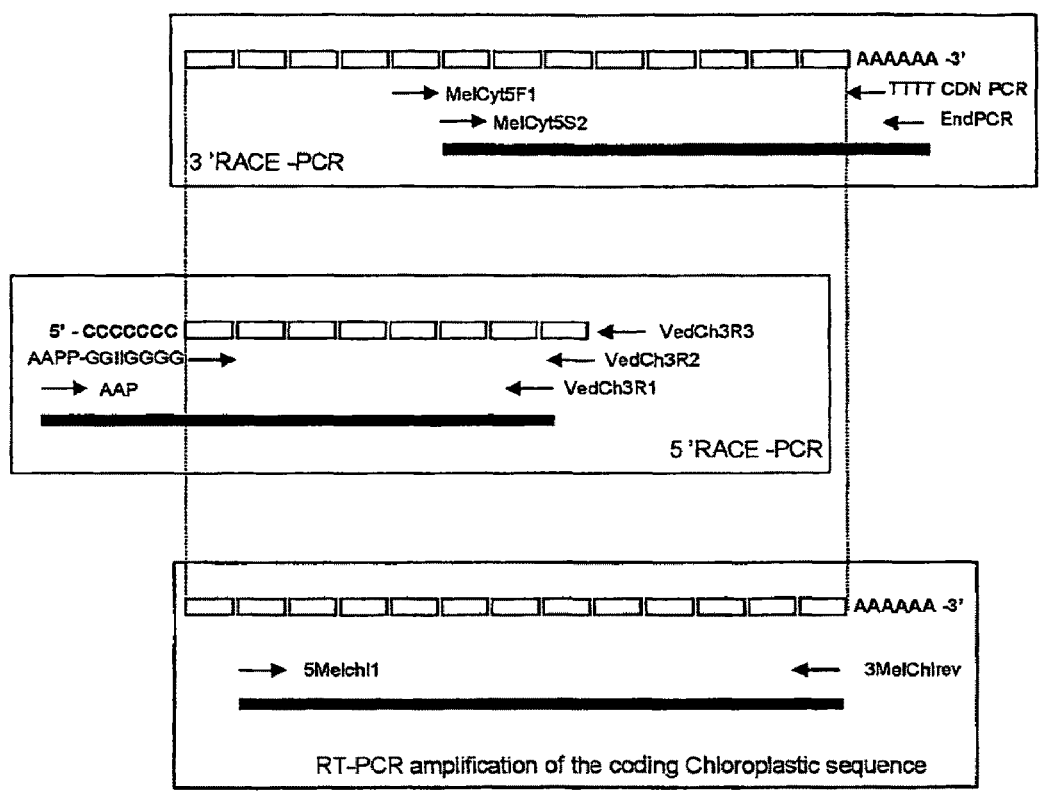
FIG. 1 is a schematic representation of the cloning method used for obtaining a cDNA coding for a CuZn superoxide dismutase from *Cucumis melo*.

These primers were built so as to contain the necessary synthetic sequences enabling their introduction in phase in a bacterial expression vector pET30a+ (available from NOVAGEN) either at the 5' BamHI or NcoI sites and at the 3' HindIII site. The global procedure for these amplification and genetic modifications are reported on FIG. 1.

The bacterial expression system enabled expression of the cloned cDNA as hybrid proteins in which the SOD or the protein variants are linked, via their N-terminus, to a His-Tag sequence.

All amplifications were carried out in a reaction volume of 50 μl containing 25 mM TAPS (pH 9.3), 50 mM KCl, 1.5 mM MgCl$_2$, 200 μM each dNTP, 10 μM of each primer, 10 ng of plasmid DNA, and 2.0 units of Goldstar DNA polymerase (Eurogentec). The respective thermocycling programs used are given in the table below and were carried out on a Gene-Amp PCR thermocycle system 9700 (Applied Biosystem).

| Table of RT-PCR amplification cycles |
|---|
| Melon 3' RACE |
| 95° c. - 3 min |
| 95° C., 25 sec |
| 55° C., 30 sec |
| 72° C., 40 sec |
| 95° C., 25 sec |
| 58° C., 30 sec |
| 72° C., 40 sec |
| Melon 5' RACE |
| 95° c. - 3 min |
| 95° C., 30 sec |
| 55° C., 30 sec |
| 72° C., 60 sec |
| 95° C., 30 sec |
| 61° C., 40 sec |
| 72° C., 50 sec |
| Melon Chloro |
| 95° c. - 3 min |
| 95° C., 40 sec |
| 57° C., 40 sec |
| 72° C., 40 sec |
| 95° C., 40 sec |

| Table of RT-PCR amplification cycles |
|---|
| 60° C., 40 sec |
| 72° C., 50 sec |
| Melon Pseudo-Cyt |
| 95° c. - 3 min |
| 95° C., 40 sec |
| 57° C., 40 sec |
| 72° C., 40 sec |
| 95° C., 40 sec |
| 60° C., 40 sec |
| 72° C., 50 sec |

The amplifications of the three protein variants "Cyt, Dur, and Vul" encoding for the human, tomato as well as melon SOD were performed according to the same protocol taking into account the variable size of each of the 5' oligonucleotide primers. Reactions were first heated at 94° C. for 5 min and submitted to 5 preliminary cycles as follow (0.45 min denaturing at 94° C., 0.55 min annealing at 56° C. and 0.55 min extension at 72° C.) and then to further 25 cycles (0.45 min denaturing at 94° C., 0.55 min annealing at 59° C. and 0.55 min extension at 72° C.).

The coding region of each previously cloned Cu—ZnSOD cDNA was amplified by PCR and the amplified 459 bp and 495 bp products were then digested with the appropriate restriction endonucleases NcoI to the 5' end and HindIII to the 3' end enabling their introduction in phase in a bacterial expression pET30a+ (available from NOVAGEN).

The nucleotide sequence of the three clones for each species (human, tomato, and melon) were determined and found to be identical to the previously acquired sequences and are presented hereunder:

For the chloroplastic or peroxisomal CuZn-SOD form (SEQ.ID No. 24)

*GATTGAATTC GATATC*ATGC AAGCAGTTCT TGCAGCTATG

GCCGCACAAT CCCTTCTCTC TGTTTCCCTT TCCAACTACA

TCGCATTGCC CCCATTCTCC AATTCTTCCT CTTCTCTTTC

TCTCACCTCT TCTTTCCATG GCGCCTCTCT CAAACTCCCT

CGCCACTCCC TCTCCCTCGC CGCCTCCGTT GCCCCCAAAC

CCCTTGCCGT CGTTGCCGCC TCCAAGAAAG CTGTCGCTGT

CCTCAAGGGA ACTTCCGACG TTGAAGGCGT TGTCACGCTC

ACCCAAGAAG ACGATGGTCC AACATCAGTC AATGTGCGTA

TTACCGGGCT CACCCCAGGT CCTCATGGAT TCCATCTTCA

TGAATTTGGA GACACAACAA ATGGATGCAT TTCTACAGGA

GCACATTTCA ATCCTAACAA GTTAACGCAT GGTGCTCCTG

AGGACGAAAT CCGACATGCG GGTGACCTGG GAAACATAAT

TGCCAATGCT GATGGAGTAG CAGAGGCAAC CATTGTAGAT

AACCAGATTC CTCTTAGCGG CCCCAATTCT GTAGTTGGAA

GAGCCTTTGT GGTACATGAG CTTGCGGATG ATCTAGGAAA

AGGAGGTCAT GAACTCAGTT TAACCACTGG CAATGCGGGT

GGAAGATTGG CATGTGGTGT TGTCGGTCTG ACTCCTGTGT

GA*CATGCAG*

For the melon pseudo cytosolic Cu—ZnSOD form (SEQ.ID No. 25):

GAC GAC GAC GAC AAG GCC ATG GTG AAA GCT GTC GCT
GTC CTC AAG GGA ACT TCC GAC GTT GAA GGC GTT GTC
ACG CTC ACC CAA GAA GAC GAT GGT CCA ACA TCA GTC
AAT GTG CGT ATT ACC GGG CTC ACC CCA GGT CCT CAT
GGA TTC CAT CTT CAT GAA TTT GGA GAC ACA ACA AAT
GGA TGC ATT TCT ACA GGA GCA CAT TTC AAT CCT AAC
AAG TTA ACG CAT GGT GCT CCT GAG GAC GAA ATC CGA
CAT GCG GGT GAC CTG GGA AAC ATA ATT GCC AAT GCT
GAT GGA GTA GCA GAG GCA ACC ATT GTA GAT AAC CAG
ATT CCT CTT AGC GGC CCC AAT TCT GTA GTT GGA AGA
GCC TTT GTG GTA CAT GAG CTT GCG GAT GAT CTA GGA
AAA GGA GGT CAT GAA CTC AGT TTA ACC ACT GGC AAT
GCG GGT GGA AGA TTG GCA TGT GGT GTT GTC GGT CTG
ACT CCT GTG TGA AGC TTG CGG CCG CAC TCG AGC ACC
ACC ACC ACC ACC ACT

For the melon pseudo cytosolic Cu—ZnSOD form with the *Triticum durum* peptide (SEQ.ID No. 26):

GAC GAC GAC GAC AAG GCC ATG GCT CAA CAA CCA CAA
GAT GCT GTC CAA CCA TTC ATG GTG AAA GCT GTC GCT
GTC CTC AAG GGA ACT TCC GAC GTT GAA GGC GTT GTC
ACG CTC ACC CAA GAA GAC GAT GGT CCA ACA TCA GTC
AAT GTG CGT ATT ACC GGG CTC ACC CCA GGT CCT CAT
GGA TTC CAT CTT CAT GAA TTT GGA GAC ACA ACA AAT
GGA TGC ATT TCT ACA GGA GCA CAT TTC AAT CCT AAC
AAG TTA ACG CAT GGT GCT CCT GAG GAC GAA ATC CGA
CAT GCG GGT GAC CTG GGA AAC ATA ATT GCC AAT GCT
GAT GGA GTA GCA GAG GCA ACC ATT GTA GAT AAC CAG
ATT CCT CTT AGC GGC CCC AAT TCT GTA GTT GGA AGA
GCC TTT GTG GTA CAT GAG CTT GCG GAT GAT CTA GGA
AAA GGA GGT CAT GAA CTC AGT TTA ACC ACT GGC AAT
GCG GGT GGA AGA TTG GCA TGT GGT GTT GTC GGT CTG
ACT CCT GTG TGA AGC TTG CGG CCG CAC TCG AGC ACC
ACC ACC ACC ACC ACT

For the melon pseudo cytosolic Cu—ZnSOD form with the *Triticum vulgare* peptide (SEQ.ID No. 27):

GAC GAC GAC GAC AAG GCC ATG GCT CAA CAA CCA TAT
CCA CAA CCA CAA CCA TTC ATG GTG AAA GCT GTC GCT
GTC CTC AAG GGA ACT TCC GAC GTT GAA GGC GTT GTC
ACG CTC ACC CAA GAA GAC GAT GGT CCA ACA TCA GTC
AAT GTG CGT ATT ACC GGG CTC ACC CCA GGT CCT CAT
GGA TTC CAT CTT CAT GAA TTT GGA GAC ACA ACA AAT
GGA TGC ATT TCT ACA GGA GCA CAT TTC AAT CCT AAC
AAG TTA ACG CAT GGT GCT CCT GAG GAC GAA ATC CGA
CAT GCG GGT GAC CTG GGA AAC ATA ATT GCC AAT GCT
GAT GGA GTA GCA GAG GCA ACC ATT GTA GAT AAC CAG
ATT CCT CTT AGC GGC CCC AAT TCT GTA GTT GGA AGA
GCC TTT GTG GTA CAT GAG CTT GCG GAT GAT CTA GGA
AAA GGA GGT CAT GAA CTC AGT TTA ACC ACT GGC AAT
GCG GGT GGA AGA TTG GCA TGT GGT GTT GTC GGT CTG
ACT CCT GTG TGA AGC TTG CGG CCG CAC TCG AGC ACC
ACC ACC ACC ACC ACT

For the Tomato cytosolic Cu—ZnSOD form (SEQ.ID No. 28):

GAC GAC GAC GAC AAG GCC ATG GTG AAG GCC GTC GCC
GTC CTT AAC AGC AGT GAA GGT GTT AGT GGC ACC ATC
CTC TTC ACT CAA GAT GGA GAT GCT CCA ACC ACA GTT
AAT GGA AAT ATT TCT GGC CTA AAA CCT GGA CTT CAT
GGC TTC CAT GTC CAT GCC CTT GGT GAT ACC ACA AAT
GGC TGT ATG TCA ACA GGA CCA CAT TAC AAT CCT GCT
GGT AAG GAG CAT GGT GCT CCT GAA GAT GAG GTG CGT
CAT GCT GGT GAT CTT GGT AAC ATC ACA GTT GGA GAA
GAT GGT ACT GCA TCT TTT ACT ATT ACC GAC AAG CAG
ATT CCT CTC ACT GGT CCA CAG TCC ATC ATT GGA AGA
GCT GTT GTT GTT CAT GCT GAT CCT GAT GAT CTT GGA
AAG GGA GGA CAT GAG CTC AGT AAA AGC ACC GGA AAT
GCT GGC GGA AGG ATT GCT TGT GGT ATT ATT GGC CTC
CAG GGT TAA AGC TTG CGG CCG CAC TCG AGC ACC ACC
ACC ACC

For the Tomato cytosolic Cu—ZnSOD form with the *Triticum durum* peptide (SEQ.ID No. 29):

GAC GAC GAC GAC AAG GCC ATG GCT CAA CAA CCA
CAA GAT GCT GTC CAA CCA TTC ATG GTG AAG GCC GTC
GCC GTC CTT AAC AGC AGT GAA GGT GTT AGT GGC ACC
ATC CTC TTC ACT CAA GAT GGA GAT GCT CCA ACC ACA
GTT AAT GGA AAT ATT TCT GGC CTA AAA CCT GGA CTT
CAT GGC TTC CAT GTC CAT GCC CTT GGT GAT ACC ACA
AAT GGC TGT ATG TCA ACA GGA CCA CAT TAC AAT CCT
GCT GGT AAG GAG CAT GGT GCT CCT GAA GAT GAG GTG

-continued
```
CGT CAT GCT GGT GAT CTT GGT AAC ATC ACA GTT GGA

GAA GAT GGT ACT GCA TCT TTT ACT ATT ACC GAC AAG

CAG ATT CCT CTC ACT GGT CCA CAG TCC ATC ATT GGA

AGA GCT GTT GTT GTT CAT GCT GAT CCT GAT GAT CTT

GGA AAG GGA GGA CAT GAG CTC AGT AAA AGC ACC GGA

AAT GCT GGC GGA AGG ATT GCT TGT GGT ATT ATT GGC

CTC CAG GGT TAA *AGC TTG CGG CCG CAC TCG AGC*

*ACC ACC ACC ACC*
```

For the Tomato cytosolic Cu—ZnSOD form with the *Triticum vulgare* peptide (SEQ.ID No. 30):

```
*GAC GAC GAC GAC AAG GCC* ATG GCT CAA CAA CCA

TAT CCA CAA CCA CAA CCA TTC ATG GTG AAG GCC GTC

GCC GTC CTT AAC AGC AGT GAA GGT GTT AGT GGC ACC

ATC CTC TTC ACT CAA GAT GGA GAT GCT CCA ACC ACA

GTT AAT GGA AAT ATT TCT GGC CTA AAA CCT GGA CTT

CAT GGC TTC CAT GTC CAT GCC CTT GGT GAT ACC ACA

AAT GGC TGT ATG TCA ACA GGA CCA CAT TAC AAT CCT

GCT GGT AAG GAG CAT GGT GCT CCT GAA GAT GAG GTG

CGT CAT GCT GGT GAT CTT GGT AAC ATC ACA GTT GGA

GAA GAT GGT ACT GCA TCT TTT ACT ATT ACC GAC AAG

CAG ATT CCT CTC ACT GGT CCA CAG TCC ATC ATT GGA

AGA GCT GTT GTT GTT CAT GCT GAT CCT GAT GAT CTT

GGA AAG GGA GGA CAT GAG CTC AGT AAA AGC ACC GGA

AAT GCT GGC GGA AGG ATT GCT TGT GGT ATT ATT GGC

CTC CAG GGT TAA *AGC TTG CGG CCG CAC TCG AGC*

*ACC ACC ACC ACC*
```

For the Human cytosolic Cu—ZnSOD form (SEQ.ID No. 31)

```
*GAC GAC GAC GAC AAG GCC* ATG GCG ACG AAG GCC

GTG TGC GTG CTG AAG GGC GAC GGC CCA GTG CAG GGC

ATC ATC AAT TTC GAG CAG AAG GAA AGT AAT GGA CCA

GTG AAG GTG TGG GGA AGC ATT AAA GGA CTG ACT GAA

GGC CTG CAT GGA TTC CAT GTT CAT GAG TTT GGA GAT

AAT ACA GCA GGC TGT ACC AGT GCA GGT CCT CAC TTT

AAT CCT CTA TCC AGA AAA CAC GGT GGG CCA AAG GAT

GAA GAG AGG CAT GTT GGA GAC TTG GGC AAT GTG ACT

GCT GAC AAA GAT GGT GTG GCC GAT GTG TCT ATT GAA

GAT TCT GTG ATC TCA CTC TCA GGA GAC CAT TGC ATC

ATT GGC CGC ACA CTG GTG GTC CAT GAA AAA GCA GAT

GAC TTG GGC AAA GGT GGA AAT GAA GAA AGT ACA AAG

ACA GGA AAC GCT GGA AGT CGT TTG GCT TGT GGT GTA

ATT GGG ATC GCC CAA *TAA AAG CTT GCG GCC GCA*

*CTC GAG CAC CAC CAC CAC*
```

For the Human cytosolic Cu—ZnSOD form with the *Triticum durum* peptide (SEQ.ID No. 32)

```
*GAC GAC GAC GAC AAG GCC* ATG GCT CAA CAA CCA

CAA GAT GCT GTC CAA CCA TTC ATG GCG ACG AAG GCC

GTG TGC GTG CTG AAG GGC GAC GGC CCA GTG CAG GGC

ATC ATC AAT TTC GAG CAG AAG GAA AGT AAT GGA CCA

GTG AAG GTG TGG GGA AGC ATT AAA GGA CTG ACT GAA

GGC CTG CAT GGA TTC CAT GTT CAT GAG TTT GGA GAT

AAT ACA GCA GGC TGT ACC AGT GCA GGT CCT CAC TTT

AAT CCT CTA TCC AGA AAA CAC GGT GGG CCA AAG GAT

GAA GAG AGG CAT GTT GGA GAC TTG GGC AAT GTG ACT

GCT GAC AAA GAT GGT GTG GCC GAT GTG TCT ATT GAA

GAT TCT GTG ATC TCA CTC TCA GGA GAC CAT TGC ATC

ATT GGC CGC ACA CTG GTG GTC CAT GAA AAA GCA GAT

GAC TTG GGC AAA GGT GGA AAT GAA GAA AGT ACA AAG

ACA GGA AAC GCT GGA AGT CGT TTG GCT TGT GGT GTA

ATT GGG ATC GCC CAA *TAA AAG CTT GCG GCC GCA*

*CTC GAG CAC CAC CAC CAC*
```

For the Human cytosolic Cu—ZnSOD form with the *Triticum vulgare* peptide (SEQ.ID No. 33)

```
*GAC GAC GAC GAC AAG GCC* ATG GCT CAA CAA CCA

TAT CCA CAA CCA CAA CCA TTC ATG GCG ACG AAG GCC

GTG TGC GTG CTG AAG GGC GAC GGC CCA GTG CAG GGC

ATC ATC AAT TTC GAG CAG AAG GAA AGT AAT GGA CCA

GTG AAG GTG TGG GGA AGC ATT AAA GGA CTG ACT GAA

GGC CTG CAT GGA TTC CAT GTT CAT GAG TTT GGA GAT

AAT ACA GCA GGC TGT ACC AGT GCA GGT CCT CAC TTT

AAT CCT CTA TCC AGA AAA CAC GGT GGG CCA AAG GAT

GAA GAG AGG CAT GTT GGA GAC TTG GGC AAT GTG ACT

GCT GAC AAA GAT GGT GTG GCC GAT GTG TCT ATT GAA

GAT TCT GTG ATC TCA CTC TCA GGA GAC CAT TGC ATC

ATT GGC CGC ACA CTG GTG GTC CAT GAA AAA GCA GAT

GAC TTG GGC AAA GGT GGA AAT GAA GAA AGT ACA AAG

ACA GGA AAC GCT GGA AGT CGT TTG GCT TGT GGT GTA

ATT GGG ATC GCC CAA *TAA AAG CTT GCG GCC GCA*

*CTC GAG CAC CAC CAC CAC*
```

The analysis of the nucleic acid sequences using computer software for the determination of ORFs and sequence alignment with known plant superoxide dismutases enabled determination of a peptide sequence that was compatible to requirements and also the peptide sequences of the variants that resulted from the genetic modifications described previously:

For the melon chloroplastic CuZn-SOD form (SEQ.ID No. 34):

```
MQAVLAAMAA QSLLSVSLSN YIALPPFSNS SSSLSLTSSF

HGASLKLPRH SLSLAASVAP KPLAVVAASK KAVAVLKGTS

DVEGVVTLTQ EDDGPTSVNV RITGLTPGPH GFHLHEFGDT

TNGCISTGAH FNPNKLTHGA PEDEIRHAGD LGNIIANADG

VAEATIVDNQ IPLSGPNSVV GRAFVVHELA DDLGKGGHEL

SLTTGNAGGR LACGVVGLTP V*
```

For the melon pseudo-cytosolic CuZnSOD form (SEQ.ID No. 35):

```
MVKAVAVLKG TSDVEGVVTL TQEDDGPTSV NVRITGLTPG

PHGFHLHEFG DTTNGCISTG AHFNPNKLTH GAPEDEIRHA

GDLGNIIANA DGVAEATIVD NQIPLSGPNS VVGRAFVVHE

LADDLGKGGH ELSLTTGNAG GRLACGVVGL TPV*
```

For the melon pseudo-cytosolic CuZnSOD form+the *Triticum durum* peptide (SEQ.ID No. 36):

```
QQPQDAVQPF MVKAVAVLKG TSDVEGVVTL TQEDDGPTSV

NVRITGLTPG PHGFHLHEFG DTTNGCISTG AHFNPNKLTH

GAPEDEIRHA GDLGNIIANA DGVAEATIVD NQIPLSGPNS

VVGRAFVVHE LADDLGKGGH ELSLTTGNAG GRLACGVVGL

TPV*
```

For the melon pseudo-cytosolic CuZnSOD form+the *Triticum vulgare* peptide (SEQ.ID No. 37):

```
QQPYPQPQPF MVKAVAVLKG TSDVEGVVTL TQEDDGPTSV

NVRITGLTPG PHGFHLHEFG DTTNGCISTG AHFNPNKLTH

GAPEDEIRHA GDLGNIIANA DGVAEATIVD NQIPLSGPNS

VVGRAFVVHE LADDLGKGGH ELSLTTGNAG GRLACGVVGL

TPV*
```

For the Tomato cytosolic Cu—ZnSOD form (SEQ.ID No. 38):

```
MVKAVAVLNS SEGVSGTILF TQDGDAPTTV NGNISGLKPG

LHGFHVHALG DTTNGCMSTG PHYNPAGKEH GAPEDEVRHA

GDLGNITVGE DGTASFTITD KQIPLTGPQS IIGRAVVVHA

DPDDLGKGGH ELSKSTGNAG GRIACGIIGL QG*
```

For the Tomato cytosolic Cu—ZnSOD form with the *Triticum durum* peptide (SEQ.ID No. 39):

```
QQPQDAVQPF MVKAVAVLNS SEGVSGTILF TQDGDAPTTV

NGNISGLKPG LHGFHVHALG DTTNGCMSTG PHYNPAGKEH

GAPEDEVRHA GDLGNITVGE DGTASFTITD KQIPLTGPQS

IIGRAVVVHA DPDDLGKGGH ELSKSTGNAG GRIACGIIGL

QG*
```

For the Tomato cytosolic Cu—ZnSOD form with the *Triticum vulgare* peptide (SEQ.ID No. 40):

```
QQPYPQPQPF MVKAVAVLNS SEGVSGTILF TQDGDAPTTV

NGNISGLKPG LHGFHVHALG DTTNGCMSTG PHYNPAGKEH

GAPEDEVRHA GDLGNITVGE DGTASFTITD KQIPLTGPQS

IIGRAVVVHA DPDDLGKGGH ELSKSTGNAG GRIACGIIGL

QG*
```

For the Human cytosolic Cu—ZnSOD form (SEQ.ID No. 41):

```
MATKAVCVLK GDGPVQGIIN FEQKESNGPV KVWGSIKGLT

EGLHGFHVHE FGDNTAGCTS AGPHFNPLSR KHGGPKDEER

HVGDLGNVTA DKDGVADVSI EDSVISLSGD HCIIGRTLVV

HEKADDLGKG GNEESTKTGN AGSRLACGVI GIAQ
```

For the Human cytosolic Cu—ZnSOD form with the *Triticum durum* peptide (SEQ.ID No. 42):

```
QQPQDAVQPF MATKAVCVLK GDGPVQGIIN FEQKESNGPV

KVWGSIKGLT EGLHGFHVHE FGDNTAGCTS AGPHFNPLSR

KHGGPKDEER HVGDLGNVTA DKDGVADVSI EDSVISLSGD

HCIIGRTLVV HEKADDLGKG GNEESTKTGN AGSRLACGVI

GIAQ
```

For the Human cytosolic Cu—ZnSOD form with the *Triticum vulgare* peptide (SEQ.ID No. 43):

```
QQPYPQPQPF MATKAVCVLK GDGPVQGIIN FEQKESNGPV

KVWGSIKGLT EGLHGFHVHE FGDNTAGCTS AGPHFNPLSR

KHGGPKDEER HVGDLGNVTA DKDGVADVSI EDSVISLSGD

HCIIGRTLVV HEKADDLGKG GNEESTKTGN AGSRLACGVI

GIAQ
```

The bacterial expression system pET30a, enable expression of the cloned cDNA as hydrid proteins in which the SOD is fused with cleavable N-terminal His-Tag sequence (His-Tag) after expression into the Rosetta (DE3) pLysS bacterial strain (Novagen).

The recombinant clones obtained, selected for each of the variant forms of Cu—ZnSOD created, were resuspended in 1 litre of rich media (Tryptone 10 g/l, Yeast extract 5 g/l, NaCl 5 g/l) supplemented with appropriate antibiotics (30 µg/ml of chloramphenicol and/or 34 µg/ml of kanamycin until the OD600 nm had risen to a value of 0.6, following incubation at 37° C. for at least 3 hours, at which point IPTG (Isopropylthiogalactopyrannoside), a lac promoter inducer that controls the expression of the protein, was added to obtain a final concentration of 1 mM and incubated for 4 to 6 further hours.

Two bacterial pellets for each preparation were resuspended (1) in 50 ml of cold PBS buffer or (2) in 50 ml of loading buffer (available from Novagen) and submitted to sonication buffer (Tris.HCl pH7.4 10 mM, EDTA 1 mM, NaCl 150 mM) for 4 successive cycles of 30 sec each at 4° C. (Vibracell 40W-20 KHz). The intracytoplasmic protein extracts were isolated by centrifugation for 20 minutes at 13000 g.

Starting from the crude protein extract, the various His-Tag SOD fusion proteins were isolated on a His-Bind quick cartridge (available under ref 70155, from NOVAGEN). The various SOD and their specific variants were then purified by a new purification step onto His-Bind quick cartridge after hydrolysis of the hybrid proteins with the recombinant Enterokinase (ref 69066, NOVAGEN).

Example 5

Melon Anti-recSOD Antibody

Having obtained the amino acid sequences of the recombinant melon SODs, a comparative analysis was carried out with other plant SODs, using Swiss Plot alignment and chose two peptide sequences 14-27 (EP1668-GV-VTLTQEDDGPTS, SEQ.ID No. 44)) and 117-131 (EP1669-HELADDLGKGGHELS, SEQ.ID No. 45) for the immunisation of rabbits in order to obtain melon specific polyclonal antibodies (Eurogentec, Belgium). The antibody EP1669 was purified on a affinity column by immunoabsorption and used at $1/2000$ in western blot analysis in order to verify the specificity of the antibody vis à vis the melon recombinant SODs produced.

For SDS-PAGE analysis, the protein extracts were heated to 95° C. for 5 minutes, and then electrophoresis was carried out on SDS polyacrylamide gel at 12%. The proteins that separated out were transferred onto an immuno-blot PVDF membrane (BIORAD). Any potential cross specificity of the antibody was revealed with the amplified-Opti4CN Goat anti-rabbit detection kit (BIORAD).

The EP 1669 antibody showed good specificity with the complete recombinant melon SOD proteins from which the immunisation peptide derived. Furthermore, it showed a cross specificity with recombinant human and tomato SOD as well as natural bovine SOD or human SOD. The antibody was thus shown to be useful as a detection tool for the experiments necessary to validate the pharmacological activity of the recombinant SOD proteins of the invention.

Example 6

Anti-Radical Activity

The melon pseudo cytosolic Cu—ZnSOD and the human or tomato cytosolic Cu—ZnSOD as well as their equivalents bearing the two different gliadin peptides are analysed for their antiradical activities. These activities are verified according to the NBT photoreduction on NATIVE-PAGE electrophoresis (Beauchamps and Fridovitch, 1971).

Example 7

Cellular Targeting

In order to demonstrate that the gliadin peptides used as targeting agents are capable as previously shown of interacting not only with HLA-DQ2 and then entering human enterocytes, but also of facilitating concomitant targeting of a protein that would be physically or chemically associated to it, the human colon carcinoma cell lines HT-29 (ATCC HTB-38) and Caco-2 (ATCC HTB-37) are grown in 10% fetal bovine serum (FBS) in Dulbecco's modified Eagle's medium (DME) supplemented with sodium pyruvate, glutamine, non-essential amino acids and penicillin/streptomycin. In some instances, cells are incubated with 100 IU/ml of IFN-γ (R&D Systems) for 48 hours in order to induce HLA Class II expression.

Gliadin Peptide Presentation Assay and Flow Cytometry

Approximately $2\times10^5$ cells are incubated at 37° C. with recombinant SOD at concentrations up to 1 mg/ml for 1-20 h. The SOD compounds tested are sterilized by filtration with 0.2 µm Millipore membrane. The cells are harvested and analysed by flow cytometry for HLA class II expression using the L243 mAb (anti-HLA DR, ATCC HB-55) followed by FITC-conjugated goat anti-mouse IgG (ICN-Cappel).

For the detection of SOD compounds at the cell surface, the cells are incubated with EP-1669 or EP-1668 antibodies (ISOCELL) and revealed with FITC-conjugated goat anti-rabbit IgG. Incubations are performed at 4° C. for 60 min after which the cells are washed three times in PBS containing 10% FBS and 0.1% sodium azide. The cells are then analyzed on a FACScan flow cytometer (Becton Dickinson).

Example 8

Annexin V Positive Cell Detection

For all the experiments reported in this part an exposure time of 48 h was used. The detection of apoptotic adherent cells was carried out by flow cytometry, using the binding of fluorescein isothiocyanate-labeled Annexin V to PS (Martin et al., 1995). After the incubation period, cell monolayers were detached with a PBS solution containing trypsin and EDTA as described before, washed in calcium-free and magnesium-free phosphate-buffered saline solution (PBS); $1\times10^6$ cells were collected by centrifugation to evaluate apoptosis in adherent cells. The evaluation of annexin V-FITC positive cells, was performed using the ApoAlert Annexin V apoptosis Kit (Clontech Laboratories, Palo Alto, Calif., USA). Cells were resuspended in 200 µl of binding buffer, and incubated for 15 min in the dark with 10 µl of annexin V-FITC (final concentration: 0.5 µg/ml) and 0.5 µg/ml propidium iodide to exclude necrotic cells. Two color cytometric (Fluorescence-Activated Cell Sorting (FACS)) analysis was performed on a Coulter Epics Elite ESP cell Sorter (Miami, Fla.) with an argon-ion laser tuned at 488 nm (Koopman et al., 1994).

Example 9

Cellular Penetration

A second fraction of cells, treated as described above, is used to prepare protein extracts of the different cellular compartments, i.e. membrane, cytoplasm, that are tested using Western blot analysis with the EP1669 and EP-1668 antibodies, in order to show that they had been translocated into the cells, and in particular, into the cellular compartments mentioned, by the targeting signal peptide.

Example 10

SOD Compounds Behave Differently on Intracellular Redox State

Control and treated cells ($5\times10^5$) are harvested and incubated in 495 µl of Hanks' balanced salt solution (pH 7.4) with hydroetidine (HE; Molecular Probes), dihydrorhodamine 123 (DHR 123; Molecular Probes) or 5-chloromethyl-2',7'-dichloro-dihydrofluoresceindiacetate (CM-$H_2$DCFDA, Molecular Probes) for detection of superoxide anion, hydrogen peroxide and GSH, respectively. After 15 min at 37° C. samples are analyzed on a cytometer as previously described.

Example 11

Cellular Activity

While it was long considered that SOD did not penetrate the cellular membrane because of its high molecular weight, only a few attempts have demonstrated that after 24 hours, a significant amount of carrier-free CuZn SOD, added exogenously, was able to mark out the cellular membrane (Edeas M A, et al. Cell Mol. Biol. 1996 vol 42 p 1137).

Nevertheless, to render the SOD enzyme more efficient in detoxifying intracellular ROS when added extracellularly, cell-permeable recombinant SOD proteins have been generated. A human CuZn-superoxide dismutase (CuZn-SOD) gene was fused with a gene fragment that encodes the 9 amino acids Tat protein transduction domain (RKKRRQRRR, SEQ ID NO 46) of HIV-1. This Tat-SOD fusion protein was shown to enter HeLa cells in a time- (10 to 60 min) and dose-dependent (0.2 to 2 µM) manner when added exogenously in a culture media. Once inside the cells, transduced Tat-SOD protein was enzymatically active and stable for 24 h. The cell viability of HeLa cells treated with paraquat, (an intracellular superoxide anion generator), was increased by transduced Tat-SOD (Kwon H Y et al. FEBS Lett. 2000 vol 485 p 163). However, in this case the fact that HIV-1 Tat transduction protein was shown to be responsible for the decrease in MnSOD expression in various cell types is noteworthy (Marecki J C, et al. 2004 Free Radic Biol Med vol 37 p 869/Porntadavity S et al. DNA cell Biol, 2005 vol 24 p 299). When the human CuZn-superoxide dismutase (CuZn-SOD) gene was fused with a gene fragment that encodes the 9 amino acids of a lysine rich peptide (KKKKKKKKK, SEQ ID NO 47) the transduction efficacy of 9Lys-SOD was more efficient than that of Tat-SOD (Park J, et al. Mol. Cells. 2002 vol 13 p 202).

It is now recognised that proteolytic peptides derived from various gliadin chains have the ability to generate significant modification and or alteration of intestinal cells in accordance with: a) their relative digestibility (proteolytic resistance), b) their relative size or sequence (proline rich regions) c) their relative concentration in cell cultures (agglutination or apoptosis), d) their relative recognition by HLA class II molecules (HLA DQ2 or DR3), e) their relative potentiality of zonulin induction.

It was shown that at least one, but not restricted thereto, specific gliadin-derived peptide (19-20 amino acids residues-LGQQQQPFPPQQPYPQPQPF-SEQ ID NO 48) sees its ability to bind efficiently to HLA DQ2 molecules drop when confronted with HLA DR3 molecules (Shidrawi. R G et al. 1998, Clin Exp Immunol vol 11, p 158). Many other peptides isolated from gliadin chains have similar abilities against HLA DQ2 or DR3 (Qiao. S W et al. 2004, J. Immunol. vol 173 p 1757) but only little is known about gliadin peptide interactions with normal class II HLA.

The early steps by which gliadin is able to cross the intestinal barrier were first established on rat epithelial intestinal cells IEC-6. Incubation of IEC-6 cells with gliadin led to reorganisation of intracellular actin filaments which was visible after only 15 minutes of gliadin incubation with a peak at 60 minutes and a return to baseline values after 2.5 hours. The temperature of +4° C. that failed to inhibit the gliadin induced F-actin change rules out the possibility that actin polymerisation is associated with gliadin endocytosis (Kwiatkowska K, et al. Bioassays 1999, vol 21 p 422). Gliadin may use another pathway inducing a zonulin release from enterocytes. Zonulin production was dependent on the gliadin concentration and detectable in cell culture supernatants as early as 15 minutes post-incubation with at least 0.1 mg/ml gliadin, reaching a peak at 30 minutes, and returning to baseline after 60 minutes. Addition of gliadin to rabbit intestinal mucosa mounted in Ussing chambers led to a reduction in Rt (Resistivity) which became significant after 30 minutes of incubation. Other authors have speculated that gliadin peptide derivatives were potent inducers of zonulin release and of concomitant increase in intestinal permeability (Clemente M G., et al. Gut. 2003 vol 52 p 218).

It was later demonstrated that gliadin interaction with the intestinal epithelium increases intestinal permeability through the release of zonulin that in turn, enables paracellular translocation of gliadin and its subsequent interaction with macrophages within intestinal submucosa leading to a pro-inflammatory response and free radical production (Thomas K E et al. 2006, J Immunol vol 176 p 2512).

The recombinant melon CuZn superoxide dismutase gene described above was fused with a gene fragment encoding a 10 amino acids peptide of A-gliadin (QQPYPQPQPF, SEQ.ID No. 01, designated hereafter as peptide 982). The Gli-SOD fusion protein was expressed and purified in *Escherichia coli*.

Production and Purification of Tagged Recombinant *Cucumis melo* Proteins (SOD and Gli-SOD) from Bacterial Clone Cultures.

The bacterial expression system pET30a enabled expression of a cloned cDNA as hybrid proteins in which the recombinant melon SOD or Gli-SOD (QQPYPQPQPF (SEQ ID NO 1)-SOD) were fused with a cleavable N-terminal His-Tag sequence (polypeptide-His$_6$-enterokinase cleavage sequence ~5 kDa) after expression in the Rosetta (DE3) pLysS bacterial strain (Novagen).

Fermentation and Induction Processes:

Fermentation is performed at 37° C. in 2 liters of YES medium supplemented with 50 µg/ml of kanamycin and 35 µg/ml of chloramphenicol until absorbance $A_{600}$ reached the value of 1 unit. IPTG was then added to a final concentration of 0.5 mM to induce protein expression. After overnight growth, cells were collected by centrifugation to carry out cell breakage at high pressure (French Press, 2 cycles: P>800 bars).

Denaturation Step:

The bulk is then denatured by progressive addition of urea leading to the final concentration of 8M buffer with Tris 20 mM pH 8.0. After complete dissolution, β-mercaptoethanol is added (final concentration 10 mM) to complete protein solubilisation at room temperature. Soluble proteins were recovered by centrifugation at 17000 g 15 minutes.

Purification Step:

Recombinant tagged proteins were isolated by affinity purification with an Immobilised Metal Affinity Chromatography (Chelating sepharose activated with $NiCl_2$ 0.25M, $Ni^{2+}$ ions) and first loaded onto the column in the equilibration buffer: Tris 20 mM, Urea 8 M, β-mercapto ethanol 10 mM pH 8.0.

In-Column Refolding Step:

Immobilised recombinant proteins were abundantly washed and partially refolded by decreasing the amount of urea, applying to the column a gradient from urea 8 M to 1.5 M (in buffer Tris 20 mM β-mercapto ethanol 10 mM pH 8.0).

To retrieve its antioxidant activity, superoxide dismutase has to recover its natural cofactors during the renaturation step. This is done by progressive fixation of Cu/Zn in a buffer consisting of NaAc 50 mM, Urea 1.5 M, $CuCl_2$ 0.1 mM, $ZnCl_2$ 0.1 mM, β-mercapto ethanol 10 mM pH 5.0.

Stabilisation of recombinant SOD folding is favoured by the formation of intramolecular disulfide bridges between the cysteine amino acids in a buffer consisting of Tris 20 mM, Urea 1.5 M, $CuCl_2$ 0.1 mM, $ZnCl_2$ 0.1 mM, GSH 1 mM, GSSG 4 mM, pH 8.0.

Elution Step:

Elution of the enriched tagged recombinant proteins from the affinity column is obtained with a buffer consisting of Tris 20 mM, Urea 1.5 M, Imidazole 0.5 M pH8.0. They are then dialysed overnight in Tris 20 mM, $CuCl_2$ 0.1 mM, $ZnCl_2$ 0.1 mM pH 8.0 before a final filtration against 0.22 µm filter, to avoid microbial growth during digestion. The protein content estimation was evaluated in the supernatant by the µBCA method.

Tag Cleavage:

The recombinant proteins are expressed as hybrid proteins in which the SOD or Gli-SOD are fused in their N-terminal part with a small protein containing the His-Tag sequence (His-Tag) via a small cleavable linker. This cleavage is achieved by incubation during 44 hours at room temperature with 2.0% enterokinase.

Purification of Folded and Sterile Recombinant SOD:

After release, the small tagging protein was removed from the recombinant SOD by a final purification step on MonoQ column equilibrated with Tris-HCl 20 mM pH 8.0 buffer and eluted with Tris-HCl 20 mM, NaCl 0.5 M pH 8.0, elution buffer.

Filtration at 0.22 µm to avoid microbial growth during digestion was carried out. The protein content estimation was evaluated in the supernatant by the µBCA method.

Figure 5:
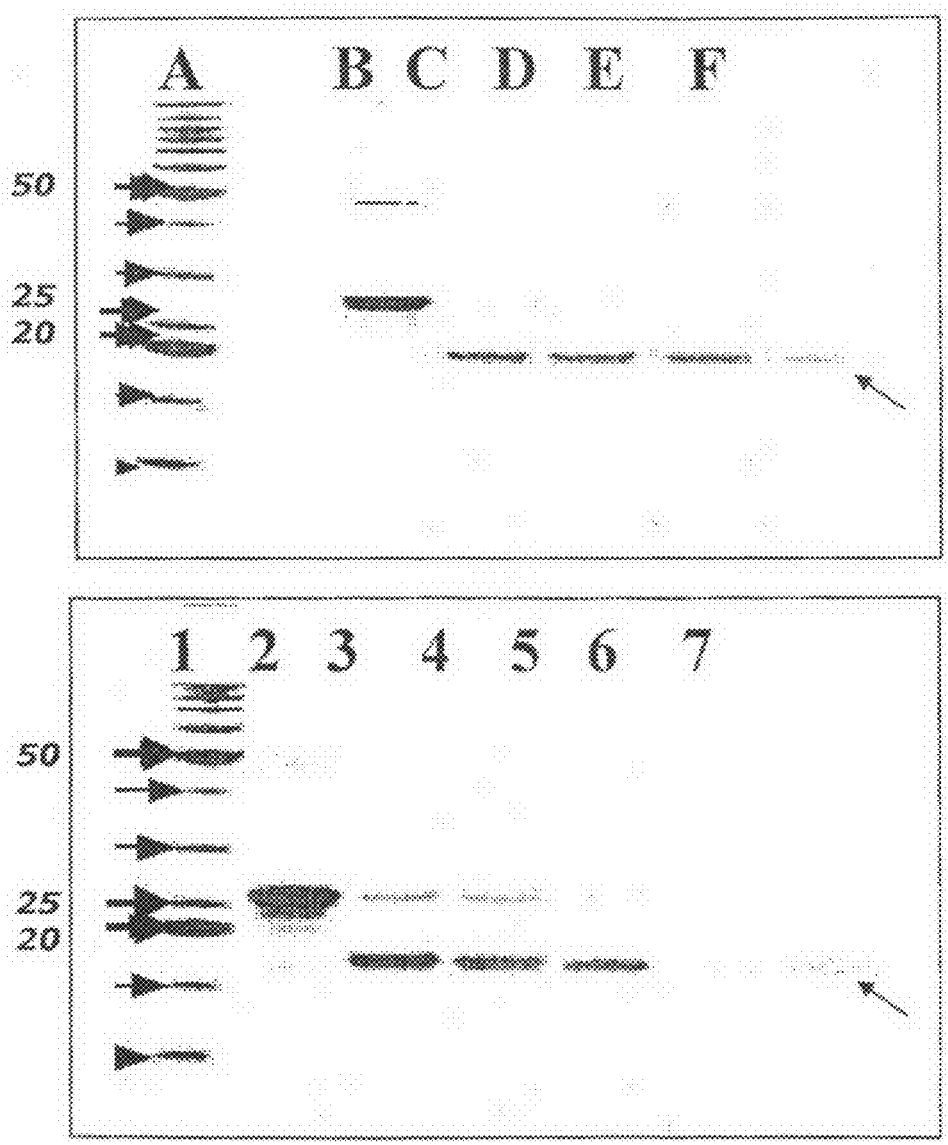
FIG. 5 is a Coomassie blue stained gel of the purification process of recombinant SOD (lanes 1-7) or recombinant fusion Gli-SOD (lanes A-F) in which:
  lanes 1 and A are molecular weight markers, known as a Benchmark Protein Ladder available from Invitrogen
  lanes 2 and B represent cleavage of the His-tag;
  lanes 3, 4, 5, 6 and C, D, E represent recombinant SOD and recombinant Gli-SOD according to the invention respectively during the successive purification steps;
  lanes 7 and F the remaining band after treatment on a MonoQ column.

The results obtained from the above purification are illustrated in FIG. 5.

Antioxidant Activity of Recombinant Refolded *Cucumis melo* SOD or Gli-SOD.

The *Cucumis melo* recombinant SOD as well as its equivalents bearing the gliadin peptide (Gli-SOD) were produced and purified according to a multiple step denaturation/renaturation protocol. While the SDS-PAGE analysis revealed a significant degree of purification, the efficacy of the refolding process is evaluated according to the recovery of its antioxidant activity. The potentiality of both recombinant proteins (*Cucumis melo* SOD and Gli-SOD) to reduce NBT on NATIVE-PAGE electrophoresis (NBT photoreduction, Beauchamps and Fridovitch, 1971) was evaluated and compared with that of the natural *Cucumis melo* extract.

The migration profile and the NBT reduction obtained on Native-PAGE electrophoresis corroborate the correct and efficient refolding of both recombinant proteins, SOD or Gli-SOD (4 000-10 000 UNBT/mg protein) which is a mandatory event to display their antioxidant activity.

Figure 6:
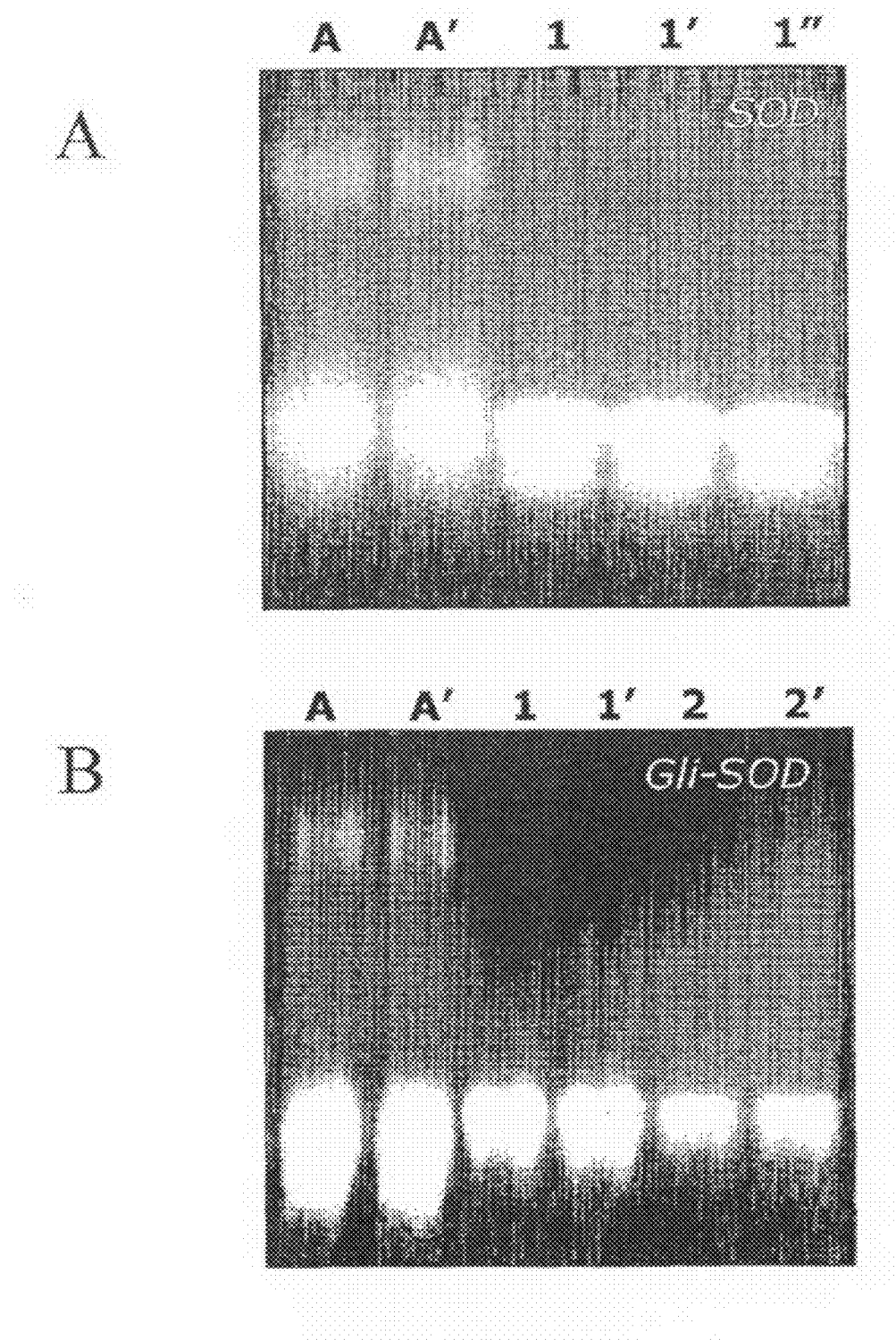

The results therefrom are illustrated in FIG. 6.

Melon Anti-recSOD Antibody:

Having obtained the amino acid sequences of the recombinant melon SOD, a comparative analysis was carried out with other plant SODs, using Swiss Plot alignment in order to select two relatively conserved peptide sequences 14-27 (EP1668-GVVTLTQEDDGPTS, SEQ ID NO 44) and 117-131 (EP1669-HELADDLGKGGHELS, SEQ ID NO 45). Both peptides were synthesized and coupled with an appropriate carrier (KLH) for the immunisation of rabbits in order to obtain plant specific polyclonal antibodies (Eurogentec, Belgium). The antibody EP1669 was purified on an affinity column by immuno-absorption and used at 1/2000 in western blot analysis in order to verify the specificity of this antibody against the natural and the melon recombinant SOD as well as a purified bovine SOD.

For SDS-PAGE analysis, the proteins were heated to 95° C. for 5 minutes, and then electrophoresis was carried out on SDS-PAGE polyacrylamide gel at 12%. The proteins that separated out were transferred onto an immuno-blot PVDF membrane (BIORAD). Any potential cross specificity of the antibody was revealed with the amplified-Opti4CN Goat anti-rabbit detection kit (BIORAD).

The EP 1669 antibody showed a cross specificity with two SODs contained into the natural melon extract or again with the purified bovine SOD. Furthermore, EP 1669 antibody showed a good specificity with the complete recombinant melon SOD protein from which the immunisation peptide derived. The antibody was thus shown to confirm the homology with at least one of the reactive SODs present in the natural extract, but also the homeology (incomplete homology) that could exist within the SOD family between various species. This antibody is a useful tool for the detection experiments necessary to validate the pharmacological activity of the recombinant SOD proteins of the invention.

The results of the above antibody binding tests are shown in FIG. 7.

Cell Culture

The human colon carcinoma cell line HT-29 (ATCC HTB-38) is grown in 10% foetal bovine serum (FBS) in Dulbecco's modified Eagle's medium (D-MEM) supplemented with GlutaMAX-1, 4.5 g/L D-Glucose, sodium pyruvate and 100 unit/ml of penicillin/streptomycin. For each experiment (n=4) approximately $2\times10^4$ cells/well were incubated for 24 hours at 37° C. in 5% $CO_2$ atmosphere. Prior to any experiment, existing culture medium was replaced by a fresh one.

After the incubation period, cell monolayers were detached with a PBS solution containing 0.05% trypsin and 0.5 mM EDTA, washed in calcium-free and magnesium-free phosphate-buffered saline solution (PBS) and collected by centrifugation. Cells were then counted in a hemocytometer by using the GUAVA PC Viacount Flex Kit and reported in cells/ml to estimate cellular proliferation.

The Effect of Non Toxic Concentrations of Gliadin Peptides

Gliadin treatment has previously been shown to exert various effects on cell growth in a concentration dependent manner. Concentrations between 50 to 200 µg/ml inhibit cell growth while concentrations up to 500 µg/ml may cause severe cell destruction. It is known that gliadin peptides may initiate their effect by first altering the oxidative balance of human intestinal cells (Dolfini E et al. 2002, *Toxicol in Vitro* vol 16 p 331).

In the current experiment, cultures are periodically sampled over a 72 hour period to assess the proliferation rate and the viability of HT-29 cells after exposure or not to various components, (a) 10 µM of gliadin peptide 982 (*Triticum vulgare*, QQPYPQPF, SEQ. ID No. 01) representing at least 100 times less than the concentration previously related to induce a significant enterocyte agglutination (De Vicenzi. M et al. 1997 *Toxicology, vol* 120 p 207) or enterocyte apoptosis (Giovannini et al. 2000, *Toxicology, vol* 145 p 63).

At such a low concentration that we tested, gliadin peptides have the ability to exert a major effect on HT-29 cell line proliferation, but exclusively at 24 hours of culture. This effect is rapidly and totally erased after 48 hours, since at this point the proliferation returns to its basal level and seems to become fully independent of the peptides' presence, probably due to peptide internalisation. It seems that gliadin peptides have to cross a concentration threshold and/or to sustain sufficient concentration on the human intestinal cell culture to lead to agglutination or further apoptosis. This is corroborated by experiments showing that after a 24 hour exposure of intestinal cells with high concentration of gliadin peptides, a significant increase in $O^{2o}$— and in $H_2O_2$ production, as well as a decrease in antioxidant enzymes are observed and precedes the gliadin peptides-induced apoptosis (Giovannini. C et al. 2003, *FEBS Letters vol* 540 p 117).

Figure 8:
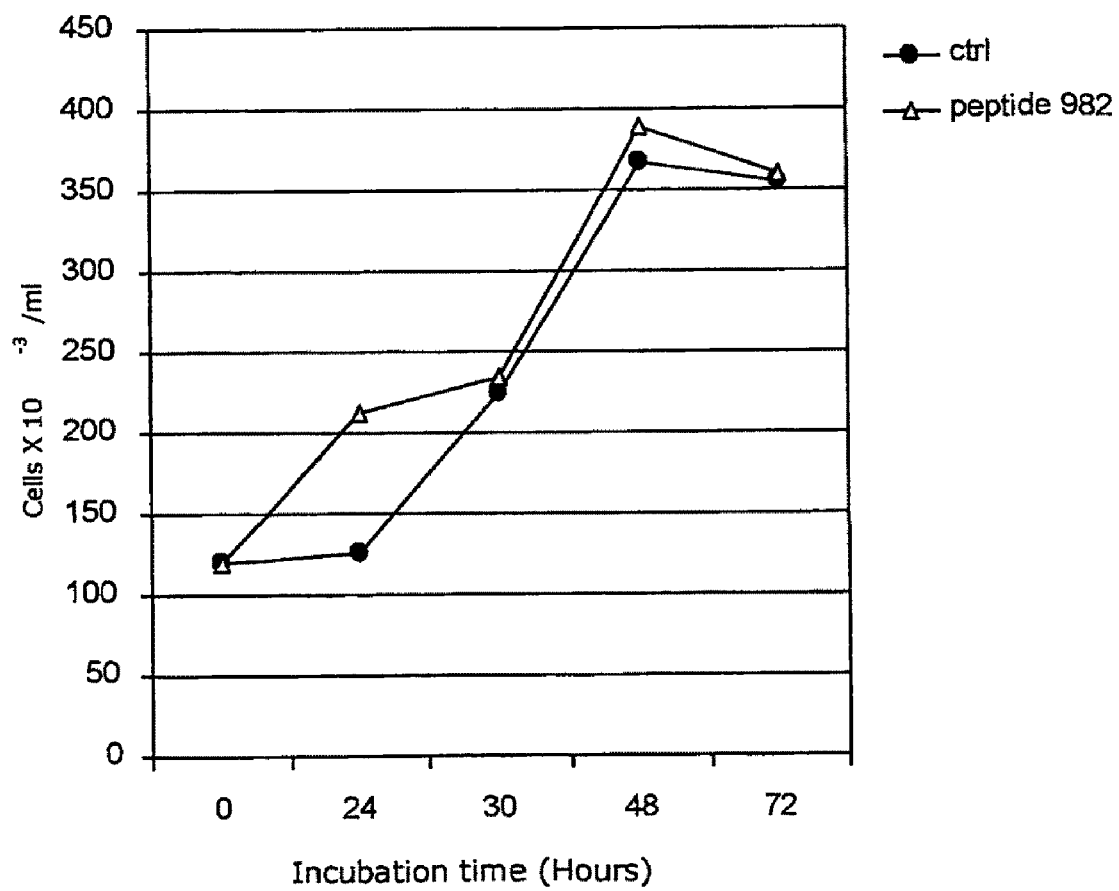
FIG. 8 is a graph of the effect of gliadin peptides on the proliferation curve of a HT29 cell line where N=4.

The results of the tests described above are illustrated in the graphic of FIG. 8.

The Minimal Active Dose of Recombinant SOD

For recombinant protein dose-response experiments, HT-29 cells were incubated with increasing concentrations of recombinant SOD or Gli-SOD (0 to 50 NBT units) for a further 48 hours.

In this experiment, two different, but parallel behaviours were observed for both recombinant SOD and Gli-SOD on HT-29 growth at 48 hours according to the lower or higher doses applied.

The growth of the HT-29 cell line is modified neither by a dose of 10 units of recombinant SOD, nor by a dose of 5 units of the recombinant Gli-SOD whereas below these values, the growth of HT-29 is slightly slowed down. For higher doses of recombinant SOD, as well as recombinant Gli-SOD, their relative level of HT-29 growth induction remains the same indicating that whatever the higher dose is, a threshold of induction may be attained. According to these results, optimal doses may be delimited between 5 to 10 units for recombinant Gli-SOD and between 10 to 25 units for the recombinant SOD.

The results of the above experiment are illustrated in FIG. 9.

The Recombinant SOD of the Invention Operate a Correction of the "Peptide Effect".

Cultures were periodically sampled over 72 hours to assess the proliferation rate and the viability of HT-29 cells after exposure or not to various components, (a) 10 units of recombinant SOD or (b) 10 units of recombinant SOD associated with 10 µM of peptide 982 or finally (c) 10 units of recombinant Gli-SOD (SOD physically linked to gliadin peptide 982).

At this concentration, neither SOD nor Gli-SOD exert any toxic effect since the proliferation curves are strictly conform and parallel to the basal curve. Moreover, there is no "peptide effect" at 24 hours of culture as expected and despite the presence of the peptide 982 at the N-terminal part of the recombinant Gli-SOD. We noticed the absence of the previously evidenced effect of gliadin peptides on HT-29 proliferation at 24 hours of culture if gliadin peptide was associated or coupled to recombinant SOD (Gli-SOD), which in turn is able to counteract the transient increase in free radical production and/or impairment of antioxidant enzymes mediated by gliadin peptides (Rivabene R et al. 1999, *Biochem Biophys Acat vol* 1453 p 152). This surprising and synergistic effect has very useful consequences in therapy and therapeutic compositions containing a functional combination, whether by association or physical or chemical linking, of the gliadin peptide and the SOD, since it shows that the expected inflammatory reaction can be mitigated and even overcome, even though the inflammatory peptide is deliberately present in the dosage form.

Figure 10:
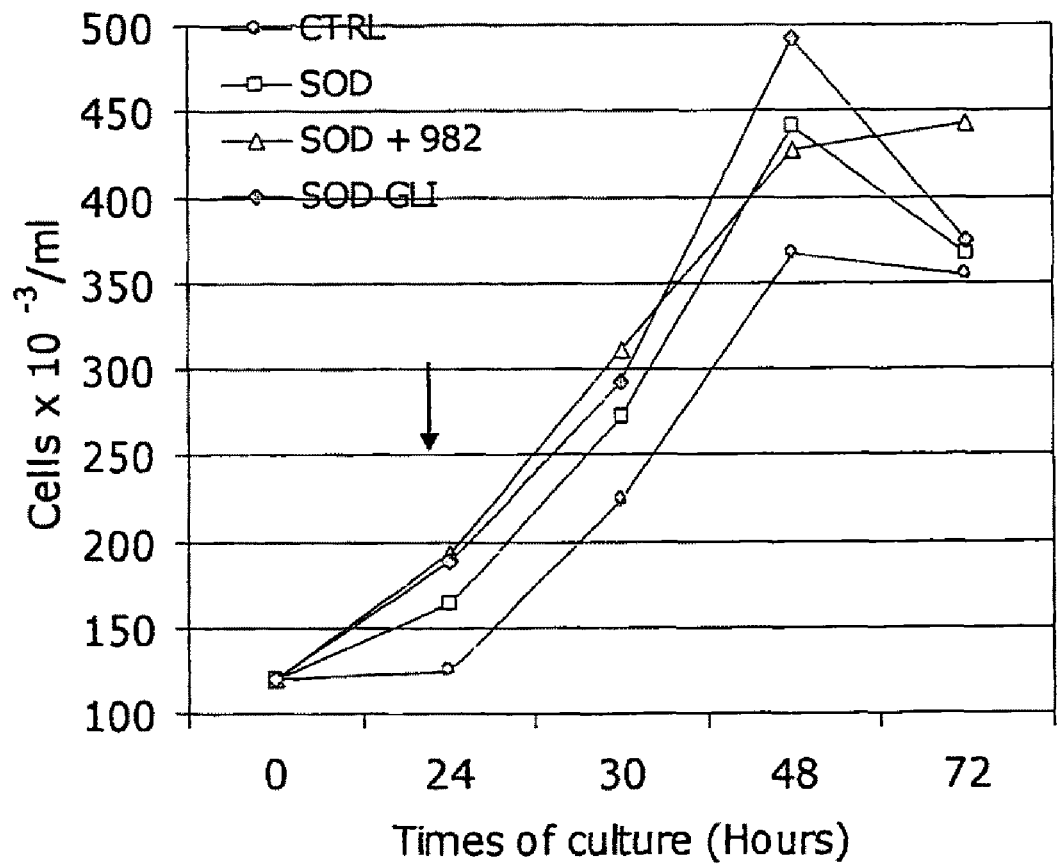
FIG. 10 is a graph of the effect of rec SOD or rec Gli-SOD according to the invention on the proliferation curve of a HT29 cell line where N=4.

The results of this experiment are handily summarised in FIG. 10.

Cell Apoptosis

Two fundamental pathways may execute apoptosis. In the first one, death ligands activate their receptors (Fas/FasLigand) resulting in the formation of a death complex which then activates caspase 8.

In the second pathway, cellular stress results in mitochondrial dysfunction with release of cytochrome C into the cytoplasm which then forms an activation complex with apoptotic proteins factor-1 and caspase 9. Both these complexes in turn activate the downstream effector caspases 3, 6 and 7 which execute the final apoptotic changes.

While digested peptides from wheat gliadin are known to induce apoptosis of intestinal epithelial cells via the CD95/Fas apoptotic pathway (Giovannini C et al. 2003, FEBS Lett. Vol 540 p 117), ROS (radical oxygen species) generated by the mixture of Xanthine/Xanthine Oxidase activate caspase-3 together with the release of Cytochrome C into the cytoplasm (Higuchi M et al. 1998, oncogene vol 17 p 2753).

First characterized as neuropeptides, orexins but also their receptors were shown to be expressed in a few peripheral tissues (Voisin T et al. 2003, *Cell Mol Life Sci vol* 60 p 72) including gastrointestinal tract (Voisin T et al. 2000, *J Pharmacol Exp Ther vol* 292 p 638). Orexins have the ability to totally suppress human colon carcinoma HT-29 cell growth after 24 hours by promoting apoptosis through cytochrome C release from mitochondria and caspase activation (Rouet-Benzineb P et al. 2004, *J Biol Chem vol* 279 p 46875).

According to the specific activities expected from the recombinant SOD or Gli-SOD of the invention to fight cellular stress and mitochondrial dysfunction, experiments were performed to verify their potent anti-apoptotic efficiencies in such inducible systems. The concentrations used for the recombinant SOD or Gli-SOD were defined according to the proliferation curves. Only 10 Units of recombinant SOD or Gli-SOD were used as that seemed sufficient enough to counteract the basal apoptotic process, whereas 50 units of recombinant SOD or Gli-SOD appeared to be more adapted to orexin or xanthine/xanthine Oxidase (X/XO)-induced apoptosis on HT-29 cells.

The Recombinant Sod Inhibited Orexin Induced Apoptosis

Apoptosis was analyzed in HT-29 cell line using the GUAVA Nexin Kit which discriminates between apoptotic and non apoptotic cells. This method utilizes annexin V Phycoerythrin to detect phopshatidylserine (PS) (Martin et al. 1995, *J Exp Med vol* 182 p 1545) on the external membrane of apoptotic cells.

After 24 hours, cell monolayers are detached with a PBS solution containing trypsin 0.05% and EDTA 0.5 mM, washed in calcium-free and magnesium-free phosphate-buffered saline solution (PBS) and apoptotic cell staining is performed and analysed with a GUAVA PCA system.

For the basal apoptotic inhibition (part A), the culture medium was replaced with fresh culture medium containing or absent 10 units of both recombinant SODs (NBT units). For the Orexin induced-apoptotic inhibition (part B), the culture medium was replaced with fresh culture medium containing 1 µM of orexin and/or 50 units of each recombinant SOD (NBT units). Results are expressed as the percentage of apoptotic annexin V-PE positive cells and are the means of four points.

Under normal conditions, apoptosis occurred spontaneously in 20% (20.5) of HT-29 cells as shown by annexin V labelling of external membrane PS. This rate dropped down to 18% (12.2% inhibition) when 10 units of recombinant melon SOD were present to finally reach 16.8% (18.1% inhibition) when 10 units of recombinant Gli-SOD were present during the culture of HT-29 cells.

In a second experiment, the potent anti-apoptotic effect of the recombinant SOD or Gli-SOD was confirmed when apoptosis was induced via orexin supplementation to the HT-29 cells culture medium. In this case, the rate of HT-29 cell going into apoptosis may be enhanced from 20% evaluated for the basal level to 40% by addition of 1 µM of Orexin in the culture medium. The rate of orexin-induced apoptosis dropped down to 34.4% (26% inhibition) when 50 units of recombinant melon SOD were present to finally reach 28.7% (54.7% inhibition) when 50 units of recombinant Gli-SOD were present during the culture of HT-29 cells.

Figure 12:
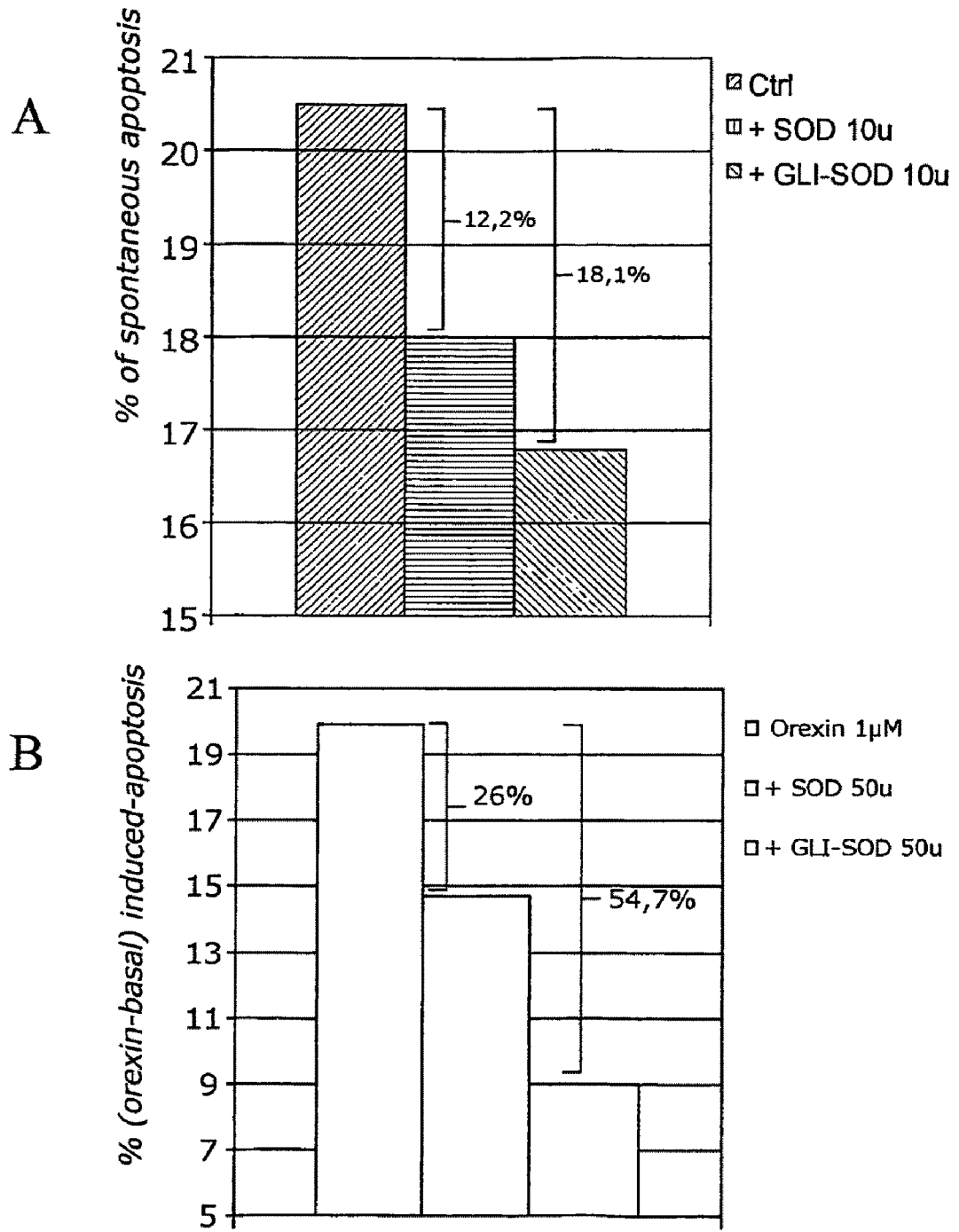
FIG. 12 is a graphic representing the effect of the SODs according to the invention on basal (A) or Orexin-induced (B) HT-29 apoptosis where N=4, using the annexin V test.

The results of this experiment are summarised in FIG. 12.

The Recombinant SOD Inhibited the X/XO Induced Apoptosis

Intestinal epithelial cell functions may be compromised by local immune and inflammatory cells such as activated macrophages (bowel disease) via production of oxygen reactive species ROS. Thus ROS may induce Fas and FasL expression in association with intestinal epithelial cell apoptosis (Denning T L et al. 2002, Free Radic Biol Med vol 33 p 1641). Xanthine oxidase in presence of xanthine generate mainly $O2-°$, a major representative of oxygen free radicals in the small intestine and may induce membrane permeability transition, calcium influx, lipid peroxidation and changes in membrane fluidity in mitochondria (Anup R et al. 1999; Indian J biochem Biophys vol 36 p 266 and Anup R et al. 2000, Br J Surg, vol 87 p 1094).

In this third experiment, tests of the potent anti-apoptotic effect of the recombinant SOD or Gli-SOD according to the invention on the possible Fas/FasL pathway via Xanthine/xanthine oxidase induction in the HT-29 cells culture medium were carried out.

In this case, the rate of HT-29 cell going into apoptosis may be enhanced from 20% evaluated for the basal level to 30% by addition of 10mU of X/XO complex in the culture medium. Addition of 50 units of recombinant melon SOD or again 50 units of recombinant Gli-SOD to the culture medium, prevented the X/XO-induced apoptotic pathway in the HT-29 cells respectively by 71% and 86%.

Figure 13:
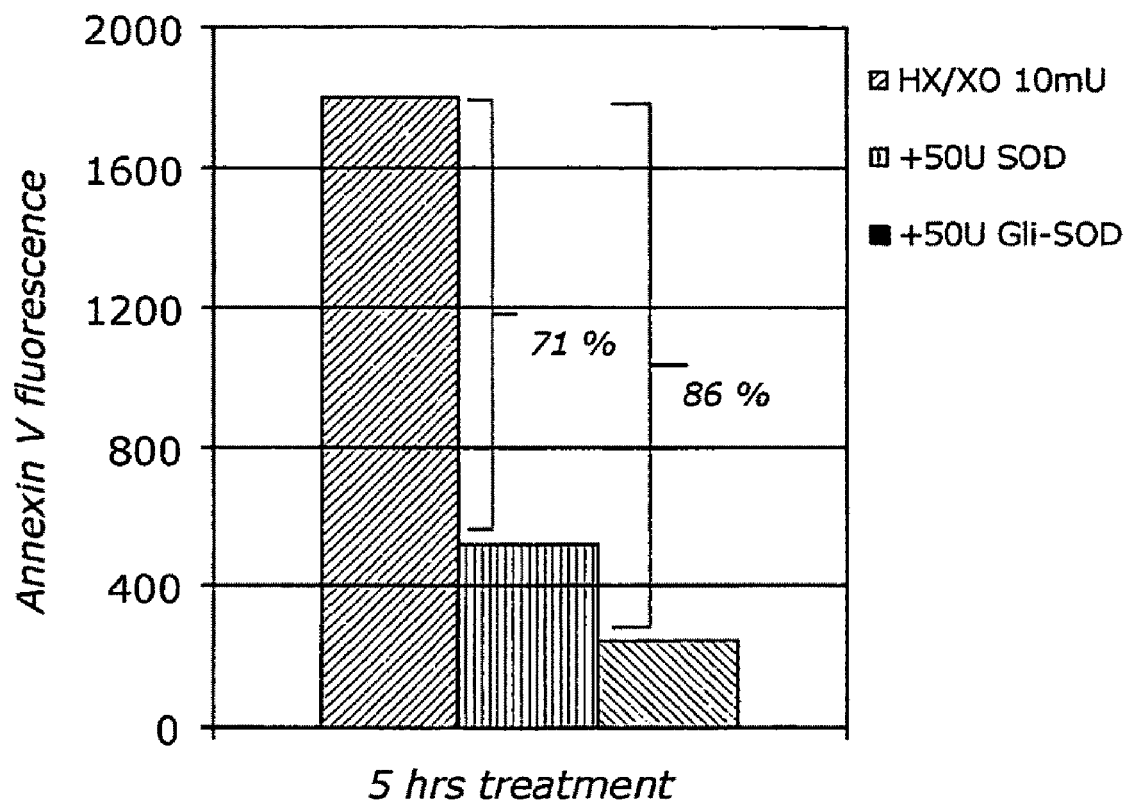
FIG. 13 illustrates a graph of the effect of recombinant SOD or Gli-SOD on Hypoxanthine/xanthine oxidase-induced HT-29 apoptosis where (N=4, annexin V test).

The results of this experiment are illustrated in the graph of FIG. 13.

The Binding of Recombinant Gli-SOD

For each experiment (n=4), approximately $15×10^3$ cells/lamella layer were incubated for 24 hours at 37° C. in 5% $CO_2$ atmosphere. Prior to any experiment, existing culture medium was replaced by a fresh one.

The cell monolayer was then incubated in a fresh medium with or without 50 units of SOD or Gli-SOD for a further 24 hours, washed in calcium-free and magnesium-free phosphate-buffered saline solution (PBS) and then analyzed by immunohistochemistry. Binding of Gli-SOD to HT-29 cells was analyzed using the EP-1669 as a first antibody (rabbit IgG anti-SOD, dilution 1/2000°) for 30 minutes followed by a second FITC-coupled antibody for further 30 minutes (goat anti-rabbit antibody, dilution 1/100). This method was chosen rather than flow cytometry because the latter technique requires that cells be harvested by trypsin treatment and collected prior to analysis, and such treatment would likely have negatively impacted the interaction between the Gli-SOD molecules and cell surfaces.

Figure 11:
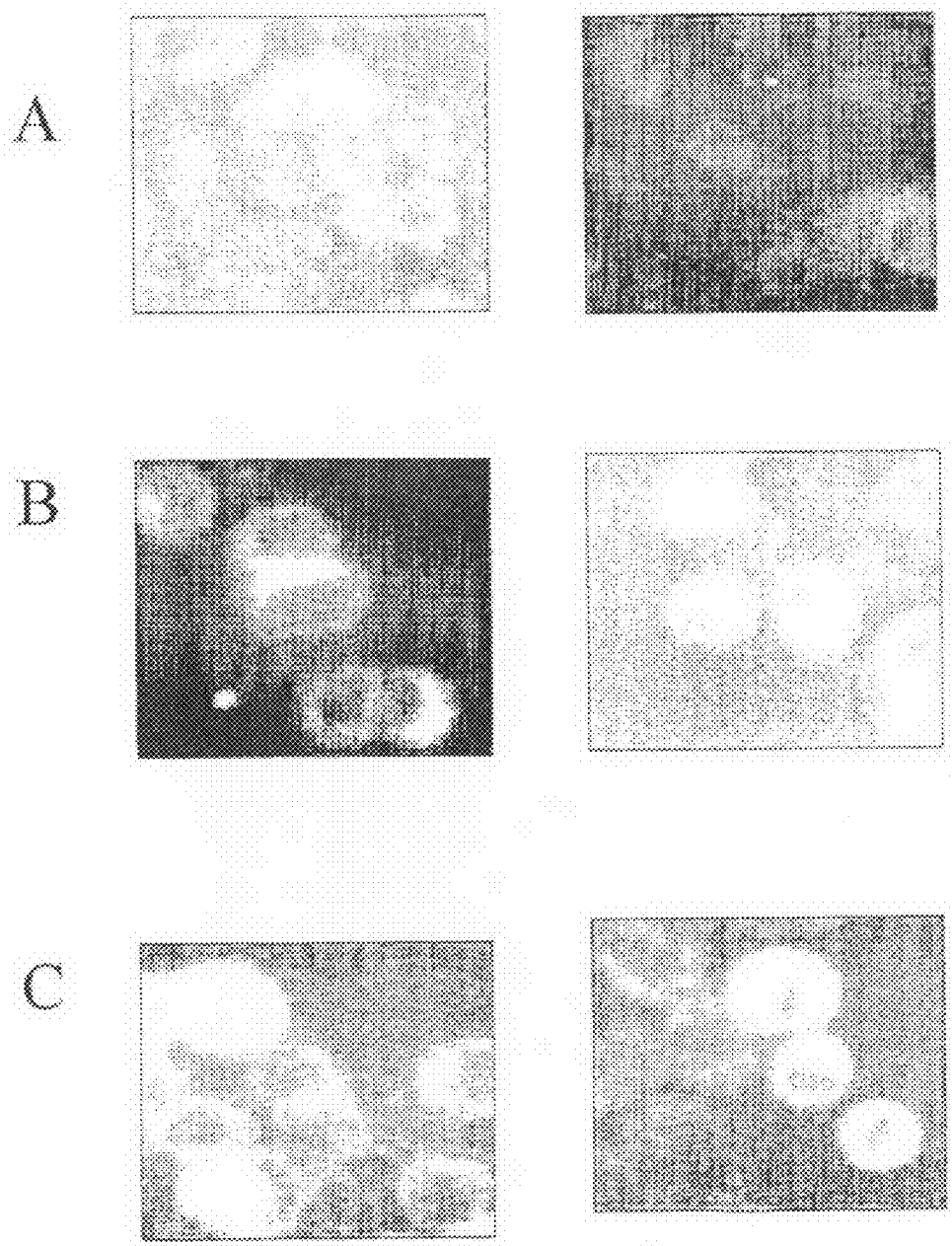
FIG. 11 is a set of FITC images showing cellular binding of SOD or Gli-SOD on HT29 cells, using the EP1669 anti-SOD antibody, where

The results of the FITC fluorescence experiments can be seen in FIG. 11, where presence of SOD in the vicinity of the cells is clearly visible, both for rec SOD, but also, and apparently to a greater extent, for the Gli-SOD.

The above experiments have demonstrated that the genetically engineered cDNAs encoding *Cucumis melo* SOD with or without *Triticum vulgare* gliadin peptide sequence in its N-terminal extremity according to the present invention may be efficiently expressed in *Escherichia coli* and produced as active molecules having antioxidant activity. In addition, while digested gliadin-peptides alone are known to induce intestinal cells agglutination or in certain circumstances cellular apoptosis, the inventors chose a shorter gliadin peptide which avoids these negative effects. It has also been shown that a physical combination or only an association of the SOD of the invention with the selected gliadin peptide is able to counteract the probable inflammatory effects of the latter.

INCORPORATION OF SEQUENCE LISTING

Incorporated herein by reference in its entirety is the Sequence Listing for the application. The Sequence Listing is disclosed on a computer-readable ASCII text file entitled, "Sequence_Listing_2028_18PCTUS.txt", created on Aug. 1, 2011. The sequence.txt file is 34.5 KB in size.

REFERENCES

1) Arentz-Hansen E H, Production of a panel of recombinant gliadins for the characterisation of T cell reactivity in coeliac disease. Gut 2000 January; 46(1):46-51
2) Baillet F, Treatment of radiofibrosis with liposomal superoxide dismutase. Preliminary results of 50 cases. Free Radic Res Commun 1986; 1(6):387-94
3) Beauchamp C. Superoxide dismutase improved assays and an assay applicable to acrylamide gels. Anal. Biochem: 1971, 44 (1) 276-287
4) Biagi F, A non-toxic analogue of a coeliac-activating gliadin peptide: a basis for immunomodulation? Aliment Pharmacol Ther 1999 July; 13(7): 945-50
5) Beckett C G, Analysis of interleukin-4 and interleukin-10 and their association with the lymphocytic infiltrate in the small intestine of patients with coeliac disease. Gut 1996 December; 39(96):818-23
6) Bolte G, Peptic-tryptic digests of gliadin: contaminating trypsin but not pepsin interferes with gastrointestinal protein binding characteristics. Clin Chim Acta 1996 Mar. 29; 247(1-2):59-70
7) Bueno P, Peroxisomal copper, zinc superoxide dismutase. Characterization of the isoenzyme from watermelon cotyledons. Plant Physiol 1995 July; 108(3):1151-60
8) Cannon R E, Cloning of cDNA for maize superoxide dismutase 2 (SOD2). Proc Natl Acad Sci USA 1987 January; 84(1):179-83
9) Cerutti P A. Prooxidant states and tumor promotion. Science 1985 Jan. 25; 227(4685):375-81
10) Chirdo F G, In vitro presentation of gliadin-derived peptides by different cell lines. Clin Chim Acta 2002 March; 317(1-2):151-8
11) Cornell H J, In vitro mucosal digestion of synthetic gliadin-derived peptides in celiac disease. J Protein Chem 1995 July; 14(5):335-9

12) Corominas M, Hypersensitivity reaction after orgotein (superoxide dismutase) administration. Allergol Immunopathol (Madr) 1990 September-October; 18(5):297-9

13) Delanian S, Successful treatment of radiation-induced fibrosis using liposomal Cu/Zn superoxide dismutase: clinical trial. Radiother. Oncol. 1994, 32 (1):12-20.

14) Diez-Gomez M L, Anaphylaxis after intra-articular injection of orgotein. Detection of an IgE-mediated mechanism. Allergy 1987 January; 42 (1):74-6

15) Freeman B A, Liposome-mediated augmentation of superoxide dismutase in endothelial cells prevents oxygen injury J Biol Chem 1983 October 25; 258(20):12534-42

16) Giovannini C, Induction of apoptosis in caco-2 cells by wheat gliadin peptides. Toxicology 2000 Apr. 7; 145(1): 63-71

17) Halliwell. B, The antioxidants of human extracellular fluids. Arch Biochem Biophys 1990 July; 280(1):1-8

18) Hidalgo I J, Characterization of the human colon carcinoma cell line (Caco-2) as a model system for intestinal epithelial permeability. Gastroenterology 1989 March; 96(3):736-49

19) Inoue, M, Expression of a hybrid Cu/Zn-type superoxide dismutase which has high affinity for heparin-like proteoglycans on vascular endothelial cells. J Biol Chem 1991 Sep. 5; 266(25):16409-14

20) Inoue M, Targeting SOD by gene and protein engineering and inhibition of free radical injury. Free Radic Res Commun 1991; 12-13 Pt 1:391-9

21) Jadot G, Anti-inflammatory activity of superoxide dismutases: studies on adjuvant induced polyarthritis in rats. Free Radic Res Commun 1986; 2(1-2):27-42

22) Jadot G, Anti-inflammatory activity of superoxide dismutases: inhibition of adriamycin induced edema in rats. Free Radic Res Commun 1986; 2(1-2):19-26

23) Jadot G, Anti-inflammatory activity of superoxide dismutases: inhibition of carrageenan induced edema in rats. Free Radic Res Commun 1986; 1(6):395-403

24) Jadot G, Clinical pharmacokinetics and delivery of bovine superoxide dismutase. Clin Pharmacokinet 1995 January; 28(1):17-25

25) Jadot G, Comparative anti-inflammatory activity of different superoxide dismutases and liposomal SOD in ischemia. Free Radic Res Commun 1987; 3(6):389-94

26) Joral A, Adverse reactions to food in adults.: J Investig Allergol Clin Immunol 1995 January-February; 5(1):47-9

27) Joral A, Systemic anaphylaxis following parenteral orgotein administration. J Investig Allergol Clin Immunol 1993 March-April; 3(2):103-4

28) Kaminaka H, Molecular cloning and characterization of a cDNA for plastidic copper/zinc-superoxide dismutase in rice (*Oryza sativa* L.). Plant Cell Physiol 1997 January; 38(1):65-9

29) Kim E J, Transcriptional and post-transcriptional regulation by nickel of sodN gene encoding nickel-containing superoxide dismutase from *Streptomyces coelicolor* Muller. Mol Microbiol 1998 January; 27(1):187-95

30) Kleber-Janke T, Use of modified BL21(DE3) *Escherichia coli* cells for high-level expression of recombinant peanut allergens affected by poor codon usage. Protein Expr Purif 2000 August; 19(3):419-24

31) Komar A A, Synonymous codon substitutions affect ribosome traffic and protein folding during in vitro translation. FEBS Lett 1999 Dec. 3; 462 (3):387-91

32) Koopman G. Annexin V for flow cytometric detection of phosphatidylserine expression on B cells undergoing apoptosis. Blood 1994, 84 (5) 1415-1420.

33) Kwiatowski J, Isolation and characterization of an iron-containing superoxide dismutase from tomato leaves, *Lycopersicon esculentum*. Eur J Biochem 1985 January 15; 146(2):459-66

34) Lavy A, Increased susceptibility to undergo lipid peroxidation of chylomicrons and low-density lipoprotein in celiac disease. Ann Nutr Metab 1993; 37(2):68-74

35) Loh E Y, Polymerase chain reaction with single-sided specificity: analysis of T cell receptor delta chain. Science 1989 Jan. 13; 243(4888): 217-20

36) Lundin K E, Gliadin-specific, HLA-DQ(alpha 1*0501, beta 1*0201) restricted T cells isolated from the small intestinal mucosa of celiac disease patients. J. Exp Med 1993 Jul. 1; 178(1):187-96

37) Martin S J. Early distribution of plasma membrane phosphatidylserine in a general feature of apoptosis regardless of the initiating stimulus: inhibition by overexpression of BcL2 and Abl. J. Exp. Med. 1995, 182 (5) 1545-1556.

38) Mayrhofer G., Absorption and presentation of antigens by epithelial cells of the small intestine: hypotheses and predictions relating to the pathogenesis of coeliac disease. Immunol Cell Biol 1995 October; 73(5):433-9

39) Mayrhofer G, Subcellular distribution of class II major histocompatibility antigens in enterocytes of the human and rat small intestine. Immunol Cell Biol 1989 August; 67 (Pt 4): 251-60

40) Michelson A M, Anti-inflammatory activity of superoxide dismutases: comparison of enzymes from different sources in different models in rats: mechanism of action. Free Radic Res Commun 1986; 2(1-2):43-56

41) Palma J M, Purification and properties of cytosolic copper, zinc superoxide dismutase from watermelon (*Citrullus vulgaris* Schrad.) cotyledons. Free Radic Res 1997 January; 26(1):83-91

42) Pathania V, Geriforte stimulates antioxidant defense system. Indian J Exp Biol 1998 April; 36(4):414-7

43) Perdereau B, [Superoxide dismutase (Cu/Zn) in cutaneous application in the treatment of radiation-induced fibrosis] Bull Cancer 1994 August; 81(8):659-69

44) Regnault C, Pharmacokinetics of superoxide dismutase in rats after oral administration. Biopharm Drug Dispos 1996 March; 17(2):165-74

45) Regnault C, Effect of encapsulation on the anti-inflammatory properties of superoxide dismutase after oral administration. Clin Chim Acta 1995 Sep. 15; 240(2):117-27

46) Rivabene R, In vitro cytotoxic effect of wheat gliadin-derived peptides on the Caco-2 intestinal cell line is associated with intracellular oxidative imbalance: implications for coeliac disease. Biochim Biophys Acta 1999 Jan. 6; 1453(1):152-60

47) Scioli J R, Cloning and characterization of a cDNA encoding the chloroplastic copper/zinc-superoxide dismutase from pea. Proc Natl Acad Sci USA 1988 October; 85(20):7661-5

48) Takeda Y, Albumin-binding superoxide dismutase with a prolonged half-life reduces reperfusion brain injury. Am J Physiol 1993 May; 264(5 Pt 2):H1708-15

49) Tatham A S, Conformational studies of peptides corresponding to the coeliac-activating regions of wheat alpha-gliadin. Biochem J 1990 Sep. 1; 270(2):313-8

50) Turrens J F, Protection against oxygen toxicity by intravenous injection of liposome-entrapped catalase and superoxide dismutase. J Clin Invest 1984 January; 73(1): 87-95

51) Vaille A, Anti-inflammatory activity of various superoxide dismutases on polyarthritis in the Lewis rat. Biochem Pharmacol 1990 Jan. 15; 39(2): 247-55
52) Varenne S, The maximum rate of gene expression is dependent on the downstream context of unfavourable codons. Biochimie 1989 November-December; 71(11-12):1221-9
53) Vouldoukis I, Fc-receptor-mediated intracellular delivery of Cu/Zn-superoxide dismutase (SOD1) protects against redox-induced apoptosis through a nitric oxide dependent mechanism. Mol Med 2000 December; 6(12): 1042-53
54) Yoo H Y, Heavy metal-mediated activation of the rat Cu/Zn superoxide dismutase gene via a metal-responsive element. Mol Gen Genet. 1999 September; 262(2):310-3
55) Zidenberg-Chem S, Dietary superoxide dismutase does not affect tissue levels. Am J Clin Nutr 1983 January; 37(1):5-7

The invention claimed is:

1. A pharmaceutical composition comprising a functionally active combination of at least one superoxide dismutase and at least one prolamine based peptide fragment, wherein the at least one superoxide dismutase and at least one prolamine based peptide fragment form a single peptide of SEQ ID NO:37.

2. A pharmaceutical composition according to claim 1, also comprising a pharmaceutically acceptable vehicle.

3. A pharmaceutical composition according to claim 1, wherein the prolamine based peptide fragment is a fragment of gliadin.

4. A pharmaceutical composition according to claim 3, wherein the prolamine based peptide fragment is a non-immunogenic gliadin.

5. A pharmaceutical composition according to claim 1, wherein the prolamine based peptide fragment is a non-immunogenic gliadin having competitive inhibiting activity with respect to immunogenic prolamine based peptides.

6. A pharmaceutical composition according to claim 1, wherein the superoxide dismutase is a homologous CuZn superoxide dismutase.

7. A pharmaceutical composition according to claim 1, wherein the superoxide dismutase is a hybrid heterologous/homologous superoxide dismutase, preferably a hybrid plant/human superoxide dismutase.

8. A pharmaceutical composition according to claim 1, wherein the superoxide dismutase is a plant superoxide dismutase.

9. A pharmaceutical composition according to claim 1, wherein the superoxide dismutase is a heterologous CuZn plant superoxide dismutase.

10. A pharmaceutical composition according to claim 1, wherein the superoxide dismutase is extracted from plants.

11. A pharmaceutical composition according to claim 1, wherein the superoxide dismutase is extracted from melon.

12. A pharmaceutical composition according to claim 1, wherein the superoxide dismutase is plant cytosolic superoxide dismutase.

13. A pharmaceutical composition according to claim 1, wherein the superoxide dismutase is a recombinant superoxide dismutase.

14. A pharmaceutical composition according to claim 1, wherein the superoxide dismutase is a recombinant superoxide dismutase that is encoded by the nucleic acid sequence SEQ ID NO 27.

15. A pharmaceutical composition according to claim 1, wherein the prolamine based peptide fragment has the amino acid sequence comprising SEQ ID NO: 1.

16. A chimeric recombinant molecule having superoxide dismutase activity comprising an amino acid sequence from a plant superoxide dismutase fused at its N-terminal to a linker amino acid sequence, wherein the molecule is SEQ ID NO:37.

17. A chimeric recombinant molecule according to claim 16, wherein the linker amino sequence comprises the amino acids methionine and valine.

18. A chimeric recombinant molecule according to claim 16, wherein the chimeric recombinant molecule comprises a prolamine based peptide fragment of SEQ ID NO: 1 fused to the N-terminal of the linker amino acid sequence.

19. A method of treatment of inflammatory pathologies by the administration of the pharmaceutical composition of claim 1.

* * * * *

UNITED STATES PATENT AND TRADEMARK OFFICE
CERTIFICATE OF CORRECTION

PATENT NO. : 8,092,794 B2
APPLICATION NO. : 12/224908
DATED : January 10, 2012
INVENTOR(S) : Alphonse Calenda It is certified that error appears in the above-identified patent and that said Letters Patent is hereby corrected as shown below:

IN THE SPECIFICATION:

Column 24, line 67:

Now reads: "QQPYPQPF, SEQ. ID No. 01"

Should read: -- QQPYPQPQPF, SEQ. ID No. 01 --

Column 25, line 66:

Now reads: "*Acat vol* 1453"

Should read: -- *Acad vol* 1453 --

Signed and Sealed this
Nineteenth Day of February, 2013

Teresa Stanek Rea
*Acting Director of the United States Patent and Trademark Office*

SEQUENCE LISTING

```
<160> NUMBER OF SEQ ID NOS: 51

<210> SEQ ID NO 1
<211> LENGTH: 10
<212> TYPE: PRT
<213> ORGANISM: Triticum vulgare

<400> SEQUENCE: 1

Gln Gln Pro Tyr Pro Gln Pro Gln Pro Phe
1               5                   10

<210> SEQ ID NO 2
<211> LENGTH: 10
<212> TYPE: PRT
<213> ORGANISM: Triticum durum

<400> SEQUENCE: 2

Gln Gln Pro Gln Asp Ala Val Gln Pro Phe
1               5                   10

<210> SEQ ID NO 3
<211> LENGTH: 57
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(57)
<223> OTHER INFORMATION: Primer

<400> SEQUENCE: 3
aagcagtggt atcaacgcag agtactttt tttttttttt tttttttttt tttttvn        57

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(23)
<223> OTHER INFORMATION: Endprimer

<400> SEQUENCE: 4
aagcagtggt atcaacgcag agt                                            23

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(20)
```

<223> OTHER INFORMATION: Primer for melon SOD coding region

<400> SEQUENCE: 5
ggtgayacma cmaatggytg                                              20

<210> SEQ ID NO 6
<211> LENGTH: 17
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(17)
<223> OTHER INFORMATION: Primer for melon coding region

<400> SEQUENCE: 6
catgckggkg ayctdgg                                                 17

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(22)
<223> OTHER INFORMATION: Primer

<400> SEQUENCE: 7
acaaaggctc ttccaactac ag                                           22

<210> SEQ ID NO 8
<211> LENGTH: 18
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(18)
<223> OTHER INFORMATION: Primer

<400> SEQUENCE: 8
gccgctaaga ggaatctg                                                18

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(22)
<223> OTHER INFORMATION: Primer

<400> SEQUENCE: 9
tggttgcctc tgctactcca tc                                           22

<210> SEQ ID NO 10
<211> LENGTH: 36
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(36)

```
<223> OTHER INFORMATION: Primer

<400> SEQUENCE: 10
ggccaggcgt cgactagtac gggggggggg gggggg                                36

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(20)
<223> OTHER INFORMATION: Primer

<400> SEQUENCE: 11
ggccaggcgt cgactagtac                                                  20

<210> SEQ ID NO 12
<211> LENGTH: 33
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(33)
<223> OTHER INFORMATION: Primer

<400> SEQUENCE: 12
atcggatcca tggcgacgaa ggccgtgtgc gtg                                   33

<210> SEQ ID NO 13
<211> LENGTH: 69
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(69)
<223> OTHER INFORMATION: Primer

<400> SEQUENCE: 13
atcggatcca tggctcaaca accacaagat gctgtccaac cattcatggc gacgaaggcc      60
gtgtgcgtg                                                              69

<210> SEQ ID NO 14
<211> LENGTH: 69
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(69)
<223> OTHER INFORMATION: Primer

<400> SEQUENCE: 14
atcggatcca tggctcaaca accatatcca caaccacaac cattcatggc gacgaaggcc      60
gtgtgcgtg                                                              69

<210> SEQ ID NO 15
<211> LENGTH: 33
<212> TYPE: DNA
<213> ORGANISM: Artificial Sequence
<220> FEATURE:
```

```
<223> OTHER INFORMATION: Oligonucleotide primer
<220> FEATURE:
<221> NAME/KEY: misc_feature
<222> LOCATION: (1)..(33)
<223> OTHER INFORMATION: Primer

<400> SEQUENCE: 15
ctcgagaagc ttttattggg cgatcccaat tac                                    33

<210> SEQ ID NO 16
<211> LENGTH: 33
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(33)
<223> OTHER INFORMATION: Primer

<400> SEQUENCE: 16
atcggatcca tggtgaaggc cgtcgccgtc ctt                                    33

<210> SEQ ID NO 17
<211> LENGTH: 69
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(69)
<223> OTHER INFORMATION: Primer

<400> SEQUENCE: 17
atcggatcca tggctcaaca accacaagat gctgtccaac cattcatggt gaaggccgtc       60
gccgtcctt                                                               69

<210> SEQ ID NO 18
<211> LENGTH: 69
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(69)
<223> OTHER INFORMATION: Primer

<400> SEQUENCE: 18
atcggatcca tggctcaaca accatatcca caaccacaac cattcatggt gaaggccgtc       60
gccgtcctt                                                               69

<210> SEQ ID NO 19
<211> LENGTH: 32
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(32)
<223> OTHER INFORMATION: Primer

<400> SEQUENCE: 19
ctcgagaagc tttaaccctg gaggccaata at                                     32

<210> SEQ ID NO 20
```

```
<211> LENGTH: 33
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(33)
<223> OTHER INFORMATION: Primer

<400> SEQUENCE: 20
atcggatcca tggtgaaagc tgtcgctgtc ctc                              33

<210> SEQ ID NO 21
<211> LENGTH: 69
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(69)
<223> OTHER INFORMATION: Primer

<400> SEQUENCE: 21
atcggatcca tggctcaaca accacaagat gctgtccaac cattcatggt gaaagctgtc    60
gctgtcctc                                                            69

<210> SEQ ID NO 22
<211> LENGTH: 69
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(69)
<223> OTHER INFORMATION: Primer

<400> SEQUENCE: 22
atcggatcca tggctcaaca accatatcca caaccacaac cattcatggt gaaagctgtc    60
gctgtcctc                                                            69

<210> SEQ ID NO 23
<211> LENGTH: 32
<212> TYPE: DNA
<213> ORGANISM: Artificial Sequence
<220> FEATURE:
<223> OTHER INFORMATION: Oligonucleotide Primer
<220> FEATURE:
<221> NAME/KEY: misc_feature
<222> LOCATION: (1)..(32)
<223> OTHER INFORMATION: Primer

<400> SEQUENCE: 23
ctcgagaagc ttcacacagg agtcagaccg ac                               32

<210> SEQ ID NO 24
<211> LENGTH: 688
<212> TYPE: DNA
<213> ORGANISM: Cucumis melo

<400> SEQUENCE: 24
gattgaattc gatatcatgc aagcagttct tgcagctatg gccgcacaat cccttctctc    60
tgtttccctt tccaactaca tgcattgcc cccattctcc aattcttcct cttctctttc    120
tctcacctct tctttccatg gcgcctctct caaactccct cgccactccc tctccctcgc   180
```

```
cgcctccgtt gccccccaaac cccttgccgt cgttgccgcc tccaagaaag ctgtcgctgt    240
cctcaaggga acttccgacg ttgaaggcgt tgtcacgctc acccaagaag acgatggtcc    300
aacatcagtc aatgtgcgta ttaccgggct cacccaggt cctcatggat tccatcttca     360
tgaatttgga gacacaacaa atggatgcat ttctacagga gcacatttca atcctaacaa    420
gttaacgcat ggtgctcctg aggacgaaat ccgacatgcg ggtgacctgg aaacataat    480 tgccaatgct gatggagtag cagaggcaac cattgtagat aaccagattc ctcttagcgg    540
ccccaattct gtagttggaa gagccttttgt ggtacatgag cttgcggatg atctaggaaa   600
aggaggtcat gaactcagtt taaccactgg caatgcgggt ggaagattgg catgtggtgt    660
tgtcggtctg actcctgtgt gactgcag                                       688
```

<210> SEQ ID NO 25
<211> LENGTH: 519
<212> TYPE: DNA
<213> ORGANISM: Cucumis melo

<400> SEQUENCE: 25

```
gacgacgacg acaaggccat ggtgaaagct gtcgctgtcc tcaagggaac ttccgacgtt     60
gaaggcgttg tcacgctcac ccaagaagac gatggtccaa catcagtcaa tgtgcgtatt    120
accgggctca ccccaggtcc tcatggattc catcttcatg aatttggaga cacaacaaat    180
ggatgcattt ctacaggagc acatttcaat cctaacaagt taacgcatgg tgctcctgag    240
gacgaaatcc gacatgcggg tgacctggga aacataattg ccaatgctga tggagtagca    300
gaggcaacca ttgtagataa ccagattcct cttagcggcc ccaattctgt agttggaaga    360
gcctttgtgg tacatgagct tgcggatgat ctaggaaaag gaggtcatga actcagttta    420
accactggca atgcgggtgg aagattggca tgtggtgttg tcggtctgac tcctgtgtga    480
agcttgcggc cgcactcgag caccaccacc accaccact                           519
```

<210> SEQ ID NO 26
<211> LENGTH: 555
<212> TYPE: DNA
<213> ORGANISM: Cucumis melo

<400> SEQUENCE: 26

```
gacgacgacg acaaggccat ggctcaacaa ccacaagatg ctgtccaacc attcatggtg     60
aaagctgtcg ctgtcctcaa gggaacttcc gacgttgaag gcgttgtcac gctcacccaa    120
gaagacgatg gtccaacatc agtcaatgtg cgtattaccg ggctcacccc aggtcctcat    180
ggattccatc ttcatgaatt tggagacaca acaaatggat gcatttctac aggagcacat    240
ttcaatccta acaagttaac gcatggtgct cctgaggacg aaatccgaca tgcgggtgac    300
ctgggaaaca taattgccaa tgctgatgga gtagcagagg caaccattgt agataaccag    360
attcctctta gcggccccaa ttctgtagtt ggaagagcct ttgtggtaca tgagcttgcg    420
gatgatctag gaaaaggagg tcatgaactc agtttaacca ctggcaatgc gggtggaaga    480
ttggcatgtg gtgttgtcgg tctgactcct gtgtgaagct gcggccgca ctcgagcacc    540 accaccacca ccact                                                     555
```

<210> SEQ ID NO 27
<211> LENGTH: 555
<212> TYPE: DNA
<213> ORGANISM: Cucumis melo

<400> SEQUENCE: 27

```
gacgacgacg acaaggccat ggctcaacaa ccatatccac aaccacaacc attcatggtg    60
aaagctgtcg ctgtcctcaa gggaacttcc gacgttgaag gcgttgtcac gctcacccaa   120
gaagacgatg gtccaacatc agtcaatgtg cgtattaccg ggctcacccc aggtcctcat   180
ggattccatc ttcatgaatt tggagacaca acaaatggat gcatttctac aggagcacat   240
ttcaatccta caagttaac gcatggtgct cctgaggacg aaatccgaca tgcgggtgac    300
ctgggaaaca taattgccaa tgctgatgga gtagcagagg caaccattgt agataaccag   360
attcctctta gcggccccaa ttctgtagtt ggaagagcct ttgtggtaca tgagcttgcg   420
gatgatctag aaaaggagg tcatgaactc agtttaacca ctggcaatgc gggtggaaga   480
ttggcatgtg gtgttgtcgg tctgactcct gtgtgaagct gcggccgca ctcgagcacc    540
accaccacca ccact                                                    555

<210> SEQ ID NO 28
<211> LENGTH: 510
<212> TYPE: DNA
<213> ORGANISM: Lycopersicon esculentum

<400> SEQUENCE: 28
gacgacgacg acaaggccat ggtgaaggcc gtcgccgtcc ttaacagcag tgaaggtgtt    60
agtggcacca tcctcttcac tcaagatgga gatgctccaa ccacagttaa tggaaatatt   120
tctggcctaa aacctggact tcatggcttc catgtccatg cccttggtga taccacaaat   180
ggctgtatgt caacaggacc acattacaat cctgctggta aggagcatgg tgctcctgaa   240
gatgaggtgc gtcatgctgg tgatcttggt aacatcacag ttgagaaga tggtactgca    300
tcttttacta ttaccgacaa gcagattcct ctcactggtc cacagtccat cattggaaga   360
gctgttgttg ttcatgctga tcctgatgat cttggaaagg gaggacatga gctcagtaaa   420
agcaccggaa atgctggcgg aaggattgct tgtggtatta ttggcctcca gggttaaagc   480
ttgcggccgc actcgagcac caccaccacc                                    510

<210> SEQ ID NO 29
<211> LENGTH: 546
<212> TYPE: DNA
<213> ORGANISM: Lycopersicon esculentum

<400> SEQUENCE: 29
gacgacgacg acaaggccat ggctcaacaa ccacaagatg ctgtccaacc attcatggtg    60
aaggccgtcg ccgtccttaa cagcagtgaa ggtgttagtg caccatcct cttcactcaa   120
gatggagatg ctccaaccac agttaatgga aatatttctg gcctaaaacc tggacttcat   180
ggcttccatg tccatgccct tggtgatacc acaaatggct gtatgtcaac aggaccacat   240
tacaatcctg ctggtaagga gcatggtgct cctgaagatg aggtgcgtca tgctggtgat   300
cttggtaaca tcacagttgg agaagatggt actgcatctt ttactattac cgacaagcag   360
attcctctca ctggtccaca gtccatcatt ggaagagctg ttgttgttca tgctgatcct   420
gatgatcttg gaaagggagg acatgagctc agtaaaagca ccggaaatgc tggcggaagg   480
attgcttgtg gtattattgg cctccagggt taaagcttgc ggccgcactc gagcaccacc   540
accacc                                                              546

<210> SEQ ID NO 30
<211> LENGTH: 546
<212> TYPE: DNA
<213> ORGANISM: Lycopersicon esculentum
```

<400> SEQUENCE: 30

```
gacgacgacg acaaggccat ggctcaacaa ccatatccac aaccacaacc attcatggtg        60
aaggccgtcg ccgtccttaa cagcagtgaa ggtgttagtg gcaccatcct cttcactcaa       120
gatggagatg ctccaaccac agttaatgga aatatttctg gcctaaaacc tggacttcat       180
ggcttccatg tccatgccct tggtgatacc acaaatggct gtatgtcaac aggaccacat       240
tacaatcctg ctggtaagga gcatggtgct cctgaagatg aggtgcgtca tgctggtgat       300
cttggtaaca tcacagttgg agaagatggt actgcatctt ttactattac cgacaagcag       360
attcctctca ctggtccaca gtccatcatt ggaagagctg ttgttgttca tgctgatcct       420
gatgatcttg gaagggagg acatgagctc agtaaaagca ccggaaatgc tggcggaagg       480
attgcttgtg gtattattgg cctccagggt taaagcttgc ggccgcactc gagcaccacc       540
accacc                                                                  546
```

<210> SEQ ID NO 31
<211> LENGTH: 516
<212> TYPE: DNA
<213> ORGANISM: Homo sapiens

<400> SEQUENCE: 31

```
gacgacgacg acaaggccat ggcgacgaag gccgtgtgcg tgctgaaggg cgacggccca        60
gtgcagggca tcatcaattt cgagcagaag gaaagtaatg gaccagtgaa ggtgtgggga       120
agcattaaag gactgactga aggcctgcat ggattccatg ttcatgagtt tggagataat       180
acagcaggct gtaccagtgc aggtcctcac tttaatcctc tatccagaaa acacggtggg       240
ccaaaggatg aagagaggca tgttggagac ttgggcaatg tgactgctga caaagatggt       300
gtggccgatg tgtctattga agattctgtg atctcactct caggagacca ttgcatcatt       360
ggccgcacac tggtggtcca tgaaaaagca gatgacttgg gcaaaggtgg aaatgaagaa       420
agtacaaaga caggaaacgc tggaagtcgt ttggcttgtg gtgtaattgg gatcgcccaa       480
taaaagcttg cggccgcact cgagcaccac caccac                                 516
```

<210> SEQ ID NO 32
<211> LENGTH: 552
<212> TYPE: DNA
<213> ORGANISM: Homo sapiens

<400> SEQUENCE: 32

```
gacgacgacg acaaggccat ggctcaacaa ccacaagatg ctgtccaacc attcatggcg        60
acgaaggccg tgtgcgtgct gaagggcgac ggcccagtgc agggcatcat caatttcgag       120
cagaaggaaa gtaatggacc agtgaaggtg tgggaagca ttaaaggact gactgaaggc       180
ctgcatggat tccatgttca tgagtttgga gataatacag caggctgtac cagtgcaggt       240
cctcacttta tcctctatc cagaaaacac ggtgggccaa aggatgaaga gaggcatgtt       300
ggagacttgg gcaatgtgac tgctgacaaa gatggtgtgg ccgatgtgtc tattgaagat       360
tctgtgatct cactctcagg agaccattgc atcattggcc gcacactggt ggtccatgaa       420
aaagcagatg acttgggcaa aggtggaaat gaagaaagta caaagacagg aaacgctgga       480
agtcgtttgg cttgtggtgt aattgggatc gcccaataaa agcttgcggc cgcactcgag       540
caccaccacc ac                                                           552
```

<210> SEQ ID NO 33
<211> LENGTH: 552
<212> TYPE: DNA

<213> ORGANISM: Homo sapiens

<400> SEQUENCE: 33

```
gacgacgacg acaaggccat ggctcaacaa ccatatccac aaccacaacc attcatggcg    60
acgaaggccg tgtgcgtgct gaagggcgac ggcccagtgc agggcatcat caatttcgag   120
cagaaggaaa gtaatggacc agtgaaggtg tggggaagca ttaaaggact gactgaaggc   180
ctgcatggat ccatgttca tgagtttgga gataatacag caggctgtac cagtgcaggt   240
cctcacttta atcctctatc cagaaaacac ggtgggccaa aggatgaaga gaggcatgtt   300
ggagacttgg gcaatgtgac tgctgacaaa gatggtgtgg ccgatgtgtc tattgaagat   360
tctgtgatct cactctcagg agaccattgc atcattggcc gcacactggt ggtccatgaa   420
aaagcagatg acttgggcaa aggtggaaat gaagaaagta caagacagg aaacgctgga   480
agtcgtttgg cttgtggtgt aattgggatc gcccaataaa agcttgcggc cgcactcgag   540
caccaccacc ac                                                        552
```

<210> SEQ ID NO 34
<211> LENGTH: 221
<212> TYPE: PRT
<213> ORGANISM: Cucumis melo

<400> SEQUENCE: 34

```
Met Gln Ala Val Leu Ala Ala Met Ala Ala Gln Ser Leu Leu Ser Val
  1               5                  10                  15
Ser Leu Ser Asn Tyr Ile Ala Leu Pro Pro Phe Ser Asn Ser Ser Ser
                 20                  25                  30
Ser Leu Ser Leu Thr Ser Ser Phe His Gly Ala Ser Leu Lys Leu Pro
             35                  40                  45
Arg His Ser Leu Ser Leu Ala Ala Ser Val Ala Pro Lys Pro Leu Ala
         50                  55                  60
Val Val Ala Ala Ser Lys Lys Ala Val Ala Val Leu Lys Gly Thr Ser
     65                  70                  75                  80
Asp Val Glu Gly Val Val Thr Leu Thr Gln Glu Asp Asp Gly Pro Thr
                 85                  90                  95
Ser Val Asn Val Arg Ile Thr Gly Leu Thr Pro Gly Pro His Gly Phe
                100                 105                 110
His Leu His Glu Phe Gly Asp Thr Thr Asn Gly Cys Ile Ser Thr Gly
            115                 120                 125
Ala His Phe Asn Pro Asn Lys Leu Thr His Gly Ala Pro Glu Asp Glu
        130                 135                 140
Ile Arg His Ala Gly Asp Leu Gly Asn Ile Ile Ala Asn Ala Asp Gly
    145                 150                 155                 160
Val Ala Glu Ala Thr Ile Val Asp Asn Gln Ile Pro Leu Ser Gly Pro
                    165                 170                 175
Asn Ser Val Gly Arg Ala Phe Val Val His Glu Leu Ala Asp Asp
                180                 185                 190
Leu Gly Lys Gly Gly His Glu Leu Ser Leu Thr Thr Gly Asn Ala Gly
            195                 200                 205
Gly Arg Leu Ala Cys Gly Val Val Gly Leu Thr Pro Val
        210                 215                 220
```

<210> SEQ ID NO 35
<211> LENGTH: 153
<212> TYPE: PRT
<213> ORGANISM: Cucumis melo

```
<400> SEQUENCE: 35

Met Val Lys Ala Val Ala Val Leu Lys Gly Thr Ser Asp Val Glu Gly
1               5                   10                  15

Val Val Thr Leu Thr Gln Glu Asp Asp Gly Pro Thr Ser Val Asn Val
            20                  25                  30

Arg Ile Thr Gly Leu Thr Pro Gly Pro His Gly Phe His Leu His Glu
        35                  40                  45

Phe Gly Asp Thr Thr Asn Gly Cys Ile Ser Thr Gly Ala His Phe Asn
    50                  55                  60

Pro Asn Lys Leu Thr His Gly Ala Pro Glu Asp Glu Ile Arg His Ala
65                  70                  75                  80

Gly Asp Leu Gly Asn Ile Ile Ala Asn Ala Asp Gly Val Ala Glu Ala
                85                  90                  95

Thr Ile Val Asp Asn Gln Ile Pro Leu Ser Gly Pro Asn Ser Val Val
            100                 105                 110

Gly Arg Ala Phe Val Val His Glu Leu Ala Asp Asp Leu Gly Lys Gly
        115                 120                 125

Gly His Glu Leu Ser Leu Thr Thr Gly Asn Ala Gly Gly Arg Leu Ala
    130                 135                 140

Cys Gly Val Val Gly Leu Thr Pro Val
145                 150

<210> SEQ ID NO 36
<211> LENGTH: 163
<212> TYPE: PRT
<213> ORGANISM: Cucumis melo

<400> SEQUENCE: 36

Gln Gln Pro Gln Asp Ala Val Gln Pro Phe Met Val Lys Ala Val Ala
1               5                   10                  15

Val Leu Lys Gly Thr Ser Asp Val Glu Gly Val Val Thr Leu Thr Gln
            20                  25                  30

Glu Asp Asp Gly Pro Thr Ser Val Asn Val Arg Ile Thr Gly Leu Thr
        35                  40                  45

Pro Gly Pro His Gly Phe His Leu His Glu Phe Gly Asp Thr Thr Asn
    50                  55                  60

Gly Cys Ile Ser Thr Gly Ala His Phe Asn Pro Asn Lys Leu Thr His
65                  70                  75                  80

Gly Ala Pro Glu Asp Glu Ile Arg His Ala Gly Asp Leu Gly Asn Ile
                85                  90                  95

Ile Ala Asn Ala Asp Gly Val Ala Glu Ala Thr Ile Val Asp Asn Gln
            100                 105                 110

Ile Pro Leu Ser Gly Pro Asn Ser Val Val Gly Arg Ala Phe Val Val
        115                 120                 125

His Glu Leu Ala Asp Asp Leu Gly Lys Gly Gly His Glu Leu Ser Leu
    130                 135                 140

Thr Thr Gly Asn Ala Gly Gly Arg Leu Ala Cys Gly Val Val Gly Leu
145                 150                 155                 160

Thr Pro Val

<210> SEQ ID NO 37
<211> LENGTH: 163
<212> TYPE: PRT
<213> ORGANISM: Cucumis melo

<400> SEQUENCE: 37
```

```
Gln Gln Pro Tyr Pro Gln Pro Gln Pro Phe Met Val Lys Ala Val Ala
1               5                   10                  15

Val Leu Lys Gly Thr Ser Asp Val Glu Gly Val Val Thr Leu Thr Gln
            20                  25                  30

Glu Asp Asp Gly Pro Thr Ser Val Asn Val Arg Ile Thr Gly Leu Thr
        35                  40                  45

Pro Gly Pro His Gly Phe His Leu His Glu Phe Gly Asp Thr Thr Asn
    50                  55                  60

Gly Cys Ile Ser Thr Gly Ala His Phe Asn Pro Asn Lys Leu Thr His
65                  70                  75                  80

Gly Ala Pro Glu Asp Glu Ile Arg His Ala Gly Asp Leu Gly Asn Ile
                85                  90                  95

Ile Ala Asn Ala Asp Gly Val Ala Glu Ala Thr Ile Val Asp Asn Gln
            100                 105                 110

Ile Pro Leu Ser Gly Pro Asn Ser Val Val Gly Arg Ala Phe Val Val
        115                 120                 125

His Glu Leu Ala Asp Asp Leu Gly Lys Gly Gly His Glu Leu Ser Leu
    130                 135                 140

Thr Thr Gly Asn Ala Gly Gly Arg Leu Ala Cys Gly Val Val Gly Leu
145                 150                 155                 160

Thr Pro Val

<210> SEQ ID NO 38
<211> LENGTH: 152
<212> TYPE: PRT
<213> ORGANISM: Lycopersicon esculentum

<400> SEQUENCE: 38

Met Val Lys Ala Val Ala Val Leu Asn Ser Ser Glu Gly Val Ser Gly
1               5                   10                  15

Thr Ile Leu Phe Thr Gln Asp Gly Asp Ala Pro Thr Thr Val Asn Gly
            20                  25                  30

Asn Ile Ser Gly Leu Lys Pro Gly Leu His Gly Phe His Val His Ala
        35                  40                  45

Leu Gly Asp Thr Thr Asn Gly Cys Met Ser Thr Gly Pro His Tyr Asn
    50                  55                  60

Pro Ala Gly Lys Glu His Gly Ala Pro Glu Asp Glu Val Arg His Ala
65                  70                  75                  80

Gly Asp Leu Gly Asn Ile Thr Val Gly Glu Asp Gly Thr Ala Ser Phe
                85                  90                  95

Thr Ile Thr Asp Lys Gln Ile Pro Leu Thr Gly Pro Gln Ser Ile Ile
            100                 105                 110

Gly Arg Ala Val Val His Ala Asp Pro Asp Leu Gly Lys Gly
        115                 120                 125

Gly His Glu Leu Ser Lys Ser Thr Gly Asn Ala Gly Gly Arg Ile Ala
    130                 135                 140

Cys Gly Ile Ile Gly Leu Gln Gly
145                 150

<210> SEQ ID NO 39
<211> LENGTH: 162
<212> TYPE: PRT
<213> ORGANISM: Lycopersicon esculentum

<400> SEQUENCE: 39

Gln Gln Pro Gln Asp Ala Val Gln Pro Phe Met Val Lys Ala Val Ala
1               5                   10                  15
```

Val Leu Asn Ser Ser Glu Gly Val Ser Gly Thr Ile Leu Phe Thr Gln
            20                  25                  30

Asp Gly Asp Ala Pro Thr Thr Val Asn Gly Asn Ile Ser Gly Leu Lys
        35                  40                  45

Pro Gly Leu His Gly Phe His Val His Ala Leu Gly Asp Thr Thr Asn
    50                  55                  60

Gly Cys Met Ser Thr Gly Pro His Tyr Asn Pro Ala Gly Lys Glu His
65                  70                  75                  80

Gly Ala Pro Glu Asp Glu Val Arg His Ala Gly Asp Leu Gly Asn Ile
                85                  90                  95

Thr Val Gly Glu Asp Gly Thr Ala Ser Phe Thr Ile Thr Asp Lys Gln
            100                 105                 110

Ile Pro Leu Thr Gly Pro Gln Ser Ile Ile Gly Arg Ala Val Val Val
        115                 120                 125

His Ala Asp Pro Asp Asp Leu Gly Lys Gly Gly His Glu Leu Ser Lys
    130                 135                 140

Ser Thr Gly Asn Ala Gly Gly Arg Ile Ala Cys Gly Ile Ile Gly Leu
145                 150                 155                 160

Gln Gly

<210> SEQ ID NO 40
<211> LENGTH: 162
<212> TYPE: PRT
<213> ORGANISM: Lycopersicon esculentum

<400> SEQUENCE: 40

Gln Gln Pro Tyr Pro Gln Pro Gln Pro Phe Met Val Lys Ala Val Ala
1               5                   10                  15

Val Leu Asn Ser Ser Glu Gly Val Ser Gly Thr Ile Leu Phe Thr Gln
            20                  25                  30

Asp Gly Asp Ala Pro Thr Thr Val Asn Gly Asn Ile Ser Gly Leu Lys
        35                  40                  45

Pro Gly Leu His Gly Phe His Val His Ala Leu Gly Asp Thr Thr Asn
    50                  55                  60

Gly Cys Met Ser Thr Gly Pro His Tyr Asn Pro Ala Gly Lys Glu His
65                  70                  75                  80

Gly Ala Pro Glu Asp Glu Val Arg His Ala Gly Asp Leu Gly Asn Ile
                85                  90                  95

Thr Val Gly Glu Asp Gly Thr Ala Ser Phe Thr Ile Thr Asp Lys Gln
            100                 105                 110

Ile Pro Leu Thr Gly Pro Gln Ser Ile Ile Gly Arg Ala Val Val Val
        115                 120                 125

His Ala Asp Pro Asp Asp Leu Gly Lys Gly Gly His Glu Leu Ser Lys
    130                 135                 140

Ser Thr Gly Asn Ala Gly Gly Arg Ile Ala Cys Gly Ile Ile Gly Leu
145                 150                 155                 160

Gln Gly

<210> SEQ ID NO 41
<211> LENGTH: 154
<212> TYPE: PRT
<213> ORGANISM: Homo sapiens

<400> SEQUENCE: 41

Met Ala Thr Lys Ala Val Cys Val Leu Lys Gly Asp Gly Pro Val Gln
1               5                   10                  15

```
Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Cys Thr Ser Ala Gly Pro His
 50                  55                  60

Phe Asn Pro Leu Ser Arg Lys His Gly Pro Lys Asp Glu Glu Arg
 65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
130                 135                 140

Leu Ala Cys Gly Val Ile Gly Ile Ala Gln
145                 150

<210> SEQ ID NO 42
<211> LENGTH: 164
<212> TYPE: PRT
<213> ORGANISM: Homo sapiens

<400> SEQUENCE: 42

Gln Gln Pro Gln Asp Ala Val Gln Pro Phe Met Ala Thr Lys Ala Val
 1               5                  10                  15

Cys Val Leu Lys Gly Asp Gly Pro Val Gln Gly Ile Ile Asn Phe Glu
                20                  25                  30

Gln Lys Glu Ser Asn Gly Pro Val Lys Val Trp Gly Ser Ile Lys Gly
            35                  40                  45

Leu Thr Glu Gly Leu His Gly Phe His Val His Glu Phe Gly Asp Asn
 50                  55                  60

Thr Ala Gly Cys Thr Ser Ala Gly Pro His Phe Asn Pro Leu Ser Arg
 65                  70                  75                  80

Lys His Gly Gly Pro Lys Asp Glu Glu Arg His Val Gly Asp Leu Gly
                85                  90                  95

Asn Val Thr Ala Asp Lys Asp Gly Val Ala Asp Val Ser Ile Glu Asp
            100                 105                 110

Ser Val Ile Ser Leu Ser Gly Asp His Cys Ile Ile Gly Arg Thr Leu
        115                 120                 125

Val Val His Glu Lys Ala Asp Asp Leu Gly Lys Gly Gly Asn Glu Glu
130                 135                 140

Ser Thr Lys Thr Gly Asn Ala Gly Ser Arg Leu Ala Cys Gly Val Ile
145                 150                 155                 160

Gly Ile Ala Gln

<210> SEQ ID NO 43
<211> LENGTH: 164
<212> TYPE: PRT
<213> ORGANISM: Homo sapiens

<400> SEQUENCE: 43

Gln Gln Pro Tyr Pro Gln Pro Gln Pro Phe Met Ala Thr Lys Ala Val
 1               5                  10                  15

Cys Val Leu Lys Gly Asp Gly Pro Val Gln Gly Ile Ile Asn Phe Glu
```

```
                20                  25                  30
Gln Lys Glu Ser Asn Gly Pro Val Lys Val Trp Gly Ser Ile Lys Gly
            35                  40                  45

Leu Thr Glu Gly Leu His Gly Phe His Val His Glu Phe Gly Asp Asn
        50                  55                  60

Thr Ala Gly Cys Thr Ser Ala Gly Pro His Phe Asn Pro Leu Ser Arg
65                  70                  75                  80

Lys His Gly Gly Pro Lys Asp Glu Glu Arg His Val Gly Asp Leu Gly
                85                  90                  95

Asn Val Thr Ala Asp Lys Asp Gly Val Ala Asp Val Ser Ile Glu Asp
            100                 105                 110

Ser Val Ile Ser Leu Ser Gly Asp His Cys Ile Ile Gly Arg Thr Leu
        115                 120                 125

Val Val His Glu Lys Ala Asp Asp Leu Gly Lys Gly Gly Asn Glu Glu
    130                 135                 140

Ser Thr Lys Thr Gly Asn Ala Gly Ser Arg Leu Ala Cys Gly Val Ile
145                 150                 155                 160

Gly Ile Ala Gln

<210> SEQ ID NO 44
<211> LENGTH: 14
<212> TYPE: PRT
<213> ORGANISM: Cucumis melo

<400> SEQUENCE: 44

Gly Val Val Thr Leu Thr Gln Glu Asp Asp Gly Pro Thr Ser
1               5                   10

<210> SEQ ID NO 45
<211> LENGTH: 15
<212> TYPE: PRT
<213> ORGANISM: Cucumis melo

<400> SEQUENCE: 45

His Glu Leu Ala Asp Asp Leu Gly Lys Gly Gly His Glu Leu Ser
1               5                   10                  15

<210> SEQ ID NO 46
<211> LENGTH: 9
<212> TYPE: PRT
<213> ORGANISM: Artificial Sequence
<220> FEATURE:
<223> OTHER INFORMATION: Tat protein transduction domain of HIV-1

<400> SEQUENCE: 46

Arg Lys Lys Arg Arg Gln Arg Arg Arg
1               5

<210> SEQ ID NO 47
<211> LENGTH: 9
<212> TYPE: PRT
<213> ORGANISM: Artificial Sequence
<220> FEATURE:
<223> OTHER INFORMATION: a lysine rich peptide

<400> SEQUENCE: 47

Lys Lys Lys Lys Lys Lys Lys Lys Lys
1               5

<210> SEQ ID NO 48
<211> LENGTH: 20
<212> TYPE: PRT
```

```
<213> ORGANISM: Artificial Sequence
<220> FEATURE:
<223> OTHER INFORMATION: gliadin-derived peptide

<400> SEQUENCE: 48

Leu Gly Gln Gln Gln Gln Pro Phe Pro Pro Gln Gln Pro Tyr Pro Gln
1               5                   10                  15

Pro Gln Pro Phe
            20

<210> SEQ ID NO 49
<211> LENGTH: 152
<212> TYPE: PRT
<213> ORGANISM: Artificial Sequence
<220> FEATURE:
<223> OTHER INFORMATION: tomato cytosolic SOD

<400> SEQUENCE: 49

Met Val Lys Ala Val Ala Val Leu Asn Ser Ser Glu Gly Val Ser Gly
1               5                   10                  15

Thr Tyr Leu Phe Thr Gln Val Gly Val Ala Pro Thr Thr Val Asn Gly
            20                  25                  30

Asn Ile Ser Gly Leu Lys Pro Gly Leu His Gly Phe His Val His Ala
        35                  40                  45

Leu Gly Asp Thr Thr Asn Gly Cys Met Ser Thr Gly Pro His Tyr Asn
    50                  55                  60

Pro Ala Gly Lys Glu His Gly Ala Pro Glu Asp Glu Val Arg His Ala
65                  70                  75                  80

Gly Asp Leu Gly Asn Ile Thr Val Gly Glu Asp Gly Thr Ala Ser Phe
                85                  90                  95

Thr Ile Thr Asp Lys Gln Ile Pro Leu Thr Gly Pro Gln Ser Ile Ile
            100                 105                 110

Gly Arg Ala Val Val Val His Ala Asp Pro Asp Asp Leu Gly Lys Gly
        115                 120                 125

Gly His Glu Leu Ser Lys Ser Thr Gly Asn Ala Gly Gly Arg Ile Ala
    130                 135                 140

Cys Gly Ile Ile Gly Leu Gln Gly
145                 150

<210> SEQ ID NO 50
<211> LENGTH: 154
<212> TYPE: PRT
<213> ORGANISM: Artificial Sequence
<220> FEATURE:
<223> OTHER INFORMATION: human SOD

<400> SEQUENCE: 50

Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95
```

-continued

```
Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150

<210> SEQ ID NO 51
<211> LENGTH: 153
<212> TYPE: PRT
<213> ORGANISM: Artificial Sequence
<220> FEATURE:
<223> OTHER INFORMATION: melon chloroplastic SOD

<400> SEQUENCE: 51

Met Val Lys Ala Val Ala Val Leu Lys Gly Thr Ser Asp Val Glu Gly
1               5                   10                  15

Val Val Thr Leu Thr Gln Glu Asp Asp Gly Pro Thr Ser Val Asn Val
            20                  25                  30

Arg Ile Thr Gly Leu Thr Pro Gly Pro His Gly Phe His Leu His Glu
            35                  40                  45

Phe Gly Asp Thr Thr Asn Gly Cys Ile Ser Thr Gly Ala His Phe Asn
    50                  55                  60

Pro Asn Lys Leu Thr His Gly Ala Pro Glu Asp Glu Ile Arg His Ala
65                  70                  75                  80

Gly Asp Leu Gly Asn Ile Ile Ala Asn Ala Asp Gly Val Ala Glu Ala
                85                  90                  95

Thr Ile Val Asp Asn Gln Ile Pro Leu Ser Gly Pro Asn Ser Val Val
            100                 105                 110

Gly Arg Ala Phe Val Val His Glu Leu Ala Asp Asp Leu Gly Lys Gly
            115                 120                 125

Gly His Glu Leu Ser Leu Thr Thr Gly Asn Ala Gly Gly Arg Leu Ala
    130                 135                 140

Cys Gly Val Val Gly Leu Thr Pro Val
145                 150
```